(12) United States Patent
Ohshima et al.

(10) Patent No.: US 6,376,535 B2
(45) Date of Patent: Apr. 23, 2002

(54) OXYGEN-CONTAINING HETEROCYCLIC COMPOUNDS

(75) Inventors: Etsuo Ohshima, Nagareyama; Koji Yanagawa, Shizuoka; Haruhiko Manabe, Shizuoka; Ichiro Miki, Shizuoka; Yoshiaki Masuda, Shizuoka, all of (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/795,093

(22) Filed: Mar. 1, 2001

Related U.S. Application Data

(63) Continuation-in-part of application No. PCT/JP99/04788, filed on Sep. 3, 1999.

(30) Foreign Application Priority Data

Sep. 3, 1998 (JP) ............................................. 10-249685
Mar. 26, 1999 (JP) ............................................. 11-082758

(51) Int. Cl.[7] ..................... A61K 31/335; C07D 319/14
(52) U.S. Cl. ........................ 514/452; 514/414; 514/450; 514/464; 514/465; 514/466; 549/305; 549/362; 549/366; 548/454
(58) Field of Search ................................ 549/305, 362, 549/366; 548/454; 514/414, 450, 456, 464, 465, 466, 452

(56) References Cited

U.S. PATENT DOCUMENTS 5,166,367 A    11/1992   Stack et al. .................. 549/289

FOREIGN PATENT DOCUMENTS

| AU | 48-510/79 | 3/1982 |
|---|---|---|
| EP | 0 257 415 | 3/1988 |
| EP | 0 771 794 | 5/1997 |
| EP | 0 839 810 | 5/1998 |
| EP | 0 943 613 | 9/1999 |
| JP | 63-179868 | 7/1988 |
| JP | 7-242543 | 9/1995 |
| JP | 7-242655 | 9/1995 |
| JP | 10-147585 | 6/1998 |
| JP | 11-49755 | 2/1999 |
| WO | 92/10494 | 6/1992 |
| WO | WO97/16433 | 5/1997 |
| WO | WO98/15532 | 4/1998 |
| WO | WO98/22455 | 5/1998 |
| WO | 99/16766 | 4/1999 |

OTHER PUBLICATIONS

Scientia Sinica (Series B), vol. XXVI, No. 12, Dec. 1988, pp. 1291–1303.
Philip Magnus, et al., "Synthesis of the Antitumor Alkaloid . . . ", Journal of American Chemical Society, vol. 120, No. 21 (1998).

Primary Examiner—Amelia Owens
(74) Attorney, Agent, or Firm—Fitzpatrick, Cella, Harper & Scinto

(57) ABSTRACT

The present invention relates to oxygen-containing heterocyclic compounds represented by the following formula (I):

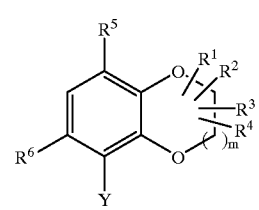

(I)

wherein m represents an integer of 0 to 4; $R^1$, $R^2$, $R^3$ and $R^4$ independently represent a hydrogen atom, substituted or unsubstituted lower alkyl, etc.; $R^5$ represents substituted or unsubstituted lower alkoxy etc.; $R^6$ represents a hydrogen atom etc.; and Y represents the following formula (II):

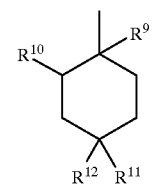

(II)

wherein $R^9$ represents cyano etc., $R^{10}$ represents a hydrogen atom etc., $R^{11}$ represents carboxy etc., and $R^{12}$ represents a hydrogen atom etc.; and the like; or
pharmaceutically acceptable salts thereof.

11 Claims, No Drawings

OXYGEN-CONTAINING HETEROCYCLIC COMPOUNDS

CROSS-REFERENCE TO RELATED APPLICATION

This is a continuation-in-part application of PCT/JP99/04788 filed on Sep. 3, 1999.

BACKGROUND OF THE INVENTION

Heretofore, it is known that the functions of numerous hormones and neurotransmitters are expressed by an increase in the concentration of adenosine 3',5'-cyclic monophosphate (cAMP) or guanosine 3',5'-cyclic monophosphate (cGMP), both of which are the secondary messengers in cells. The cellular concentrations of cAMP and cGMP are controlled by the generation and decomposition thereof, and their decomposition is carried out by phosphodiesterase (PDE). Therefore, when PDE is inhibited, the concentrations of these secondary cellular messengers increase. Up to the present, 8 kinds of PDE isozymes have been found, and the isozyme-selective PDE inhibitors are expected to exhibit pharmaceutical effect based on their physiological significance and distribution in vivo [TiPS, 11, 150 (1990), ibid., 12, 19 (1991), and Biochemical & Biophysical Research Communications, 250, 751 (1998)].

It is known that the activation of inflammatory leukocytes can be suppressed by increasing the concentration of the cellular CAMP. The extraordinary activation of leukocytes causes secretion of inflammatory cytokines such as tumor necrosis factor (TNF), and expression of the cellular adhesion molecules such as intercellular adhesion molecules (ICAM), followed by cellular infiltration [J. Mol. Cell. Cardiol., 12 (Suppl. II), S61 (1989)].

It is known that the contraction of a respiratory smooth muscle can be suppressed by increasing the concentration of the cellular cAMP (T. J. Torphy in Directions for New Anti-Asthma Drugs, eds S. R. O'Donell and C. G. A. Persson, 1988, 37, Birkhauser-Verlag). The extraordinary contraction of a respiratory smooth muscle is a main symptom of bronchial asthma. Infiltration of inflammatory-leukocytes such as neutrophils is observed in lesions of organopathy associated with ischemia-reperfusion such as myocardial ischemia. It has been found that the type IV PDE (PDE IV) mainly participates in the decomposition of cAMP in these inflammatory cells and tracheal smooth muscle cells. Therefore, the inhibitors selective for PDE IV are expected to have therapeutic and/or preventive effect on inflammatory diseases, respiratory obstructive diseases, and ischemic diseases.

The PDE IV inhibitors are expected to prevent the progress and spread of the inflammatory reaction transmitted by inflammatory cytokines such as TNF$\alpha$ and interleukin (IL)-8, because the PDE IV inhibitors suppress the secretion of these cytokines by increasing the concentration of cAMP. For example, TNF$\alpha$ is reported to be a factor of insulin-resistant diabetes because it declines the phosphorylating mechanism of insulin receptors in muscle and fat cells [J. Clin. Invest., 94, 1543 (1994)]. Similarly, it is suggested that the PDE IV inhibitors may be useful for autoimmune diseases such as rheumatoid arthritis, multiple sclerosis, and Crohn's disease because TNF$\alpha$ participates in the onset and progress of these diseases [Nature Medicine, 1, 211 (1995) and ibid., 1, 244 (1995)].

Further, participation of TNF$\alpha$ in the fatigued feeling after dialysis and that of patients suffering from cancer has been also reported [International Journal of Artificial Organs, 21, 83 (1998) and Oncology Nursing Forum, 19, 419 (1992)]. Accordingly, a PDE IV inhibitor can be expected to be effective for improvement in fatigue, malaise, and the like.

It has been reported that a drug which increases cAMP promotes the healing of wounds [The 68th Annual Meeting of Japan Pharmacological Society (in Nagoya), Presentation P3-116 (1995)].

PDE-IV inhibitors exhibit a therapeutic effect to carcinomatous osteopenia model, sciatic nerve excision model and ovariectomic model which are animal models for osteoporosis and their possibility as a therapeutic agent for osteoporosis is suggested [Jpn. J. Pharmacol., 79, 477 (1999)].

Relaxation of ureter has been known to promote the excretion of calculus while a PDE IV inhibitor suppresses the vermicular movement of ureter, and therefore, there is a suggestion for the probability that it is effective for the therapy and/or prevention of urinary calculus [J. Urol., 160, 920 (1998)].

Japanese Published Unexamined Patent Application Nos. 95/242543 and 95/242655 disclose 1,4-benzodioxane derivatives as a therapeutic agent for hepatic diseases. WO 92/10494 discloses 1,4-benzodioxane derivatives having an antagonistic action to serotonin $(5HT)_3$ receptors.

In U.S. Pat. No. 5,166,367, 1,4-benzodioxane derivatives having an anti-hallucination action are disclosed.

In Japanese Published Unexamined Patent Application No. 88/179868, 1,4-benzodioxane derivatives having a vasodilating action are disclosed.

AU 521225 discloses 1,4-benzodioxane derivatives as intermediates for the synthesis of cinnamoylpiperazine.

WO 98/22455 discloses 1,4-benzodioxane derivatives having PDE IV inhibitory activity.

SUMMARY OF THE INVENTION

The present invention relates to oxygen-containing heterocyclic compounds which have phosphodiesterase (PDE) IV inhibitory activity and which are useful as a therapeutic agent for inflammatory allergic diseases such as bronchial asthma, allergic rhinitis, atopic dermatitis and nephritis; autoimmune diseases such as chronic obstructive pulmonary disease, rheumatism, multiple sclerosis, Crohn's disease, psoriasis and systemic lupus erythematosus; diseases of the central nervous system such as depression, amnesia and dementia; organopathy associated with ischemia-reperfusion caused by cardiac failure, shock and cerebrovascular disease, and the like; insulin-resistant diabetes; wounds; AIDS; osteoporosis; urinary calculus; urinary incontinence and the like; and as a recuperative agent for fatigue, malaise and the like.

DETAILED DESCRIPTION OF THE INVENTION

Novel and useful PDE IV inhibitors are expected to have a preventive or therapeutic effect to diseases of a broad range. An object of the present invention is to provide novel oxygen-containing heterocyclic compounds having a bronchodilating or an anti-inflammatory action due to the presence of a PDE IV-selective inhibiting action so that CAMP concentrations in cells are increased.

The present invention relates to oxygen-containing heterocyclic compounds represented by the following formula (I):

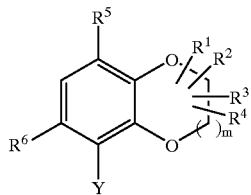

(I)

wherein m represents an integer of 0 to 4;

$R^1$, $R^2$, $R^3$ and $R^4$ independently represent a hydrogen atom, substituted or unsubstituted lower alkyl, substituted or unsubstituted cycloalkyl, polycycloalkyl, substituted or unsubstituted lower alkoxycarbonyl, substituted or unsubstituted lower alkanoyl, substituted or unsubstituted lower alkanoyloxy, cyano, hydroxy, substituted or unsubstituted lower alkoxy, substituted or unsubstituted lower alkenyl, substituted or unsubstituted cycloalkenyl, substituted or unsubstituted aryl, a substituted or unsubstituted aromatic hetecyclic group, substituted or unsubstituted aralkyl, or —$CONR^7R^8$ (wherein $R^7$ and $R^8$ independently represent a hydrogen atom, substituted or unsubstituted lower alkyl, substituted or unsubstituted lower alkanoyl, substituted or unsubstituted cycloalkyl, substituted or unsubstituted aryl, a substituted or unsubstituted aromatic heterocyclic group or substituted or unsubstituted aralkyl, or $R^7$ and $R^8$ are combined to represent a substituted or unsubstituted heterocyclic group together with the adjacent nitrogen atom); two groups present on the same carbon atom among $R^1$, $R^2$, $R^3$ and $R^4$ are combined to represent a saturated Spiro carbon ring together with the said carbon atom; two groups present on the adjacent carbon atoms among $R^1$, $R^2$, $R^3$ and $R^4$ are combined to represent a saturated carbon ring together with the said adjacent two carbon atoms; two groups present on the adjacent carbon atoms among $R^1$, $R^2$, $R^3$ and $R^4$ are combined to represent a single bond (forming a double bond together with the already-existing bond)

$R^5$ represents hydroxy, or substituted or unsubstituted lower alkoxy;

$R^6$ represents a hydrogen atom or halogen;

Y represents the following formula (II):

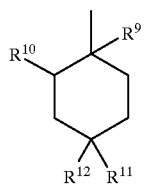

(II)

wherein $R^9$ represents cyano, ethynyl or carbamoyl, and $R^{10}$ represents a hydrogen atom, or $R^9$ and $R^{10}$ are combined to represent a single bond (forming a double bond together with the already-existing bond), $R^{11}$ represents hydroxy, formyl, substituted or unsubstituted lower alkoxy, substituted or unsubstituted tetrazolyl, —$NR^{13}R^{14}$ (wherein $R^{13}$ and $R^{14}$ independently represent a hydrogen atom, substituted or unsubstituted lower alkyl, substituted or unsubstituted lower alkanoyl, substituted or unsubstituted cycloalkyl, substituted or unsubstituted aryl, a substituted or unsubstituted aromatic heterocyclic group or substituted or unsubstituted aralkyl, or $R^{13}$ and $R^{14}$ are combined to represent a substituted or unsubstituted heterocyclic group together with the adjacent nitrogen atom), —$COOR^{15}$ (wherein $R^{15}$ represents a hydrogen atom, or substituted or unsubstituted lower alkyl), —$CONR^{16}R^{17}$ (wherein $R^{16}$ and $R^{17}$ independently represent a hydrogen atom, substituted or unsubstituted lower alkyl, substituted or unsubstituted lower alkanoyl, substituted or unsubstituted cycloalkyl, substituted or unsubstituted aryl, a substituted or unsubstituted aromatic heterocyclic group, or substituted or unsubstituted aralkyl, or $R^{16}$ and $R^{17}$ are combined to represent a substituted or unsubstituted heterocyclic group together with the adjacent nitrogen atom), or —$CH_2COOR^{18}$ (wherein $R^{18}$ represents a hydrogen atom or substituted or unsubstituted lower alkyl), $R^{12}$ represents a hydrogen atom, or substituted or unsubstituted lower alkoxy, or $R^{11}$ and $R^{12}$ are combined together to represent —$OCH_2(CH_2)_pO$— (wherein p represents an integer of 1 to 3), —$CR^{19}R^{20}O$— (wherein $R^{19}$ and $R^{20}$ independently represent a hydrogen atom or cyano), =$CHOR^{21}$ (wherein $R^{21}$ represents substituted or unsubstituted lower alkyl, substituted or unsubstituted lower alkenyl, or substituted or unsubstituted aralkyl), =$CHCOOR^{22}$ (wherein $R^{22}$ represents a hydrogen atom, or substituted or unsubstituted lower alkyl) or =O; the following formula (III):

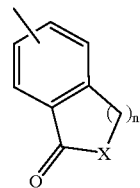

(III)

wherein n represents an integer of 0 to 4, X represents $CH_2$, $NR^{23}$ (wherein $R^{23}$ represents a hydrogen atom, substituted or unsubstituted lower alkyl, substituted or unsubstituted lower alkanoyl, substituted or unsubstituted cycloalkyl, substituted or unsubstituted aryl, a substituted or unsubstituted aromatic heterocyclic group, or substituted or unsubstituted aralkyl) or O; the following formula (IV):

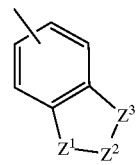

(IV)

wherein $Z^1$—$Z^2$—$Z^3$ represents O—N=CH, S—N=CH, O—CH=CH, S—CH=CH, N=CH—S, N=CH—O, C(=O)—NH—NH, C(=O)—N=N, C(=O)—$CH_2$—C(=O), C(=O)—$NR^a$—C(=O) (wherein $R^a$ represents a hydrogen atom, substituted or unsubstituted lower alkyl, or substituted or unsubstituted aralkyl) or $CH_2$—$NR^b$—C(=O) (wherein $R^b$ represents a hydrogen atom, substituted or unsubstituted lower alkyl, or substituted or unsubstituted aryl); 2,1,3-benzothiadiazolyl; or 2,1,3-benzofurazanyl; or pharmaceutically acceptable salts thereof.

The present invention relates to oxygen-containing heterocyclic compounds wherein Y in the formula (I) is the formula (II) or pharmaceutically acceptable salts thereof. Among the above, oxygen-containing heterocyclic compounds wherein $R^9$ is cyano or pharmaceutically acceptable salts thereof are preferred.

In the present invention, oxygen-containing heterocyclic compounds wherein m is 0 to 2 in the formula (I) or pharmaceutically acceptable salts thereof, oxygen-containing heterocyclic compounds wherein all of $R^1$, $R^2$, $R^3$ and $R^4$ are hydrogen atoms or pharmaceutically acceptable salts thereof and oxygen-containing heterocyclic compounds wherein one group among $R^1$, $R^2$, $R^3$ and $R^4$ is substituted or unsubstituted lower alkyl while other three groups are hydrogen atoms or pharmaceutically acceptable salts thereof are preferred examples as well.

Further, in the above-mentioned compounds group, oxygen-containing heterocyclic compounds wherein $R^{11}$ represents carboxy or hydroxy, or $R^{11}$ and $R^{12}$ are combined together to represent =O or pharmaceutically acceptable salts thereof are preferred as well.

Furthermore, oxygen-containing heterocyclic compounds wherein Y in the formula (I) is the formula (III) or pharmaceutically acceptable salts thereof are preferred as well. Still further, among the above, oxygen-containing heterocyclic compounds wherein n is 1 or pharmaceutically acceptable salts thereof and oxygen-containing heterocyclic compounds wherein X is $CH_2$ or pharmaceutically acceptable salts thereof are preferred.

The present invention further relates to a pharmaceutical composition comprising an effective amount of at least one oxygen-containing heterocyclic compound represented by the formula (I) together with a pharmaceutically acceptable carrier or diluent.

The present invention furthermore relates to a method of inhibiting phosphodiesterase (PDE) IV, which comprises administering an effective dose of at least one oxygen-containing heterocyclic compound represented by the formula (I) or a pharmaceutically acceptable salt thereof.

Hereinafter, the compounds represented by the formula (I) are referred to as a compound (I). The same applies to the compounds of other formula numbers.

In the definitions of the groups in the formula (I), the lower alkyl and the lower alkyl moiety of the lower alkoxy, the lower alkanoyl, the lower alkanoyloxy and the lower alkoxycarbonyl include straight-chain or branched alkyl groups having 1 to 8 carbon atom(s) such as methyl, ethyl, propyl, isopropyl, butyl, isobutyl, sec-butyl, tert-butyl, pentyl, hexyl, heptyl and octyl; the cycloalkyl includes cycloalkyl groups having 3 to 10 carbon atoms such as cyclopropyl, cyclobutyl, cyclopentyl, cyclohexyl, cycloheptyl, cyclooctyl, cyclononyl and cyclodecyl; and the polycycloalkyl includes polycycloalkyl groups having 5 to 12 carbon atoms such as bicyclo[3.2.1]octyl, bicyclo[4.3.2]undecyl, adamantyl and noradamantyl. The lower alkenyl includes straight-chain or branched alkenyl groups having 2 to 8 carbon atoms such as vinyl, 1-propenyl, allyl, methacryl, 1-butenyl, crotyl, pentenyl, isoprenyl, hexenyl, heptenyl and octenyl; and the cycloalkenyl includes cycloalkenyl groups having 4 to 10 carbon atoms such as cyclobutenyl, cyclopentenyl, cyclohexenyl, cycloheptenyl, cyclooctenyl, cyclononenyl and cyclodecenyl. The aryl includes phenyl and naphthyl for example; and the aralkyl includes aralkyl groups having 7 to 15 carbon atoms such as benzyl, phenethyl, benzhydryl and naphthylmethyl. The aromatic heterocyclic group includes 5- or 6-membered monocyclic aromatic heterocyclic groups having 1 to 2 oxygen atom(s), 5- or 6-membered monocyclic aromatic heterocyclic groups having 1 to 2 sulfur atom(s), 5- or 6-membered monocyclic aromatic heterocyclic groups having 1 to 4 nitrogen atom(s), condensed bicyclic aromatic heterocyclic groups consisting of 5- and 6-membered rings and condensed bicyclic aromatic heterocyclic groups consisting of 6- and 6-membered rings, where oxygen, sulfur and nitrogen may be mixedly present therein. Specific examples thereof include furyl, thienyl, pyridyl, pyrazinyl, pyrimidinyl, pyridazinyl, quinolyl, isoquinolyl, phthalazinyl, quinazolinyl, quinoxalinyl, naphthylidinyl, pyrrolyl, pyrazolyl, imidazolyl, triazolyl, tetrazolyl, thiazolyl, oxazolyl, indolyl, indazolyl, benzimidazolyl, benzotriazolyl and purinyl.

The heterocyclic group which is formed together with the adjacent nitrogen atom includes 5-, 6- or 7-membered monocyclic heterocyclic groups and condensed heterocyclic groups consisting of 6- and 6-membered rings, such as pyrrolidinyl, piperidino, piperazinyl, morpholino, thiomorpholino, homopiperidino, homopiperazinyl, tetrahydropyridyl, tetrahydroquinolyl and tetrahydroisoquinolyl.

The saturated spiro carbon ring which is formed by two groups present on the same carbon atom together with the said carbon atom and the saturated carbon ring which is formed by two groups present on the adjacent carbon atoms together with the said two carbon atoms include those having 3 to 10 carbon atoms such as cyclopropane, cyclobutane, cyclopentane, cyclohexane, cycloheptane, cyclooctane, cyclononane and cyclodecane. Halogen includes fluorine, chlorine, bromine and iodine atoms.

The substituents in the substituted lower alkyl, the substituted lower alkoxy, the substituted lower alkoxycarbonyl, the substituted lower alkanoyl, the substituted lower alkanoyloxy, the substituted lower alkenyl, the substituted cycloalkyl and the substituted cycloalkenyl are the same or different 1 to 3 substituent(s), such as lower alkyl, lower alkenyl, cyano, cycloalkyl, cycloalkenyl, hydroxy, lower alkoxy, carboxy and halogen where the lower alkyl, the lower alkenyl, the cycloalkyl, the cycloalkenyl, the lower alkoxy and the halogen each have the same meanings as defined above.

The substituents in the substituted aryl, the substituted tetrazolyl, the substituted aromatic heterocyclic group, the substituted heterocyclic group which is formed together with the adjacent nitrogen atom and the substituted aralkyl are the same or different 1 to 3 substituent(s), such as substituted or unsubstituted lower alkyl, hydroxy, lower alkoxy, lower alkanoyl, lower alkoxycarbonyl, carboxy, carbamoyl, trifluoromethyl, amino, mono- or di-lower alkyl-substituted amino, cyano, nitro and halogen. The lower alkyl, the lower alkyl moiety of the lower alkoxy, the lower alkanoyl, the lower alkoxycarbonyl and the mono- or di-lower alkyl-substituted amino and the halogen each have the same meanings as defined above where the substituent(s) in the substituted lower alkyl has/have the same meaning(s) as defined above.

The pharmaceutically acceptable salts of the compound (I) include pharmaceutically acceptable acid addition salts, metal salts, ammonium salts, and organic amine addition salts.

The pharmaceutically acceptable acid addition salts of the compound (I) include inorganic acid addition salts such as a hydrochloride, a sulfate, a nitrate, and a phosphate, and organic acid addition salts such as an acetate, a maleate, a fumarate, and a citrate; the pharmaceutically acceptable metal salts include alkali metal salts such as a sodium salt and a potassium salt, alkaline earth metal salts such as a magnesium salt and a calcium salt, an aluminium salt, and a zinc salt; the pharmaceutically acceptable ammonium salts include ammonium and tetramethylammonium; and the pharmaceutically acceptable organic amine addition salts include an addition salt with morpholine or piperidine.

Processes for preparing the compound (I) are described below.

Producing method: The compound (I) can be obtained according to the following process.

Process 1

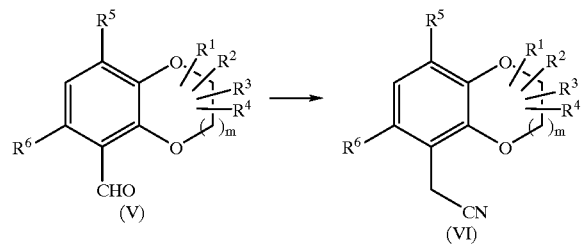

(In the formulae, m, $R^1$, $R^2$, $R^3$, $R^4$, $R^5$ and $R^6$ have the same meanings as defined above.)

The starting compound (V) can be obtained by a known method [Khimiya Geterotsiklicheskikh Soedinenii, 12, 1614 (1982), etc.] or by a method similar thereto.

After the formyl group of the compound (V) is directly converted to the corresponding halogenated methyl derivative or after the formyl group of the compound (V) is reduced and the resulting hydroxymethyl derivative is converted to the corresponding halide or sulfonate derivative, it is reacted with a metal cyanide whereupon the compound (VI) can be obtained.

The compound (V) is reacted with one equivalent to a large excess of trialkylsilyl halide or triarylsilane halide, or with one equivalent to a large excess of a halogenated salt and one equivalent to a large excess of trimethylsilyl chloride in an inert solvent at the temperature between −50° C. and the boiling point of the used solvent for 5 minutes to 5 hours, followed by treatment with one equivalent to a large excess of a reducing agent at the temperature between −50° C. and the boiling point of the used solvent for 5 minutes to 48 hours, whereupon the corresponding halide can be obtained.

Alternatively, the compound (V) is treated with one equivalent to a large excess of a reducing agent in an inert solvent at the temperature between −50° C. and the boiling point of the used solvent for 5 minutes to 48 hours whereby the corresponding hydroxylmethyl derivative is obtained. The resulting hydroxylmethyl derivative is reacted with one equivalent to a large excess of a halogenating agent in an inert solvent at the temperature between −30° C. and the boiling point of the used solvent for 5 minutes to 120 hours to give the corresponding halide.

Alternatively, the resulting hydroxymethyl derivative is treated with one equivalent to a large excess of an alkylsulfonyl chloride or an arylsulfonyl chloride in the presence of one equivalent to a large excess of a base in an inert solvent at the temperature between −30° C. and the boiling point of the used solvent for 5 minutes to 120 hours whereby the corresponding sulfonate derivative is obtained.

The resulting halide or sulfonate derivative is treated with one equivalent to a large excess of a metal cyanide in an insert solvent at the temperature between −30° C. and the boiling point of the used solvent for 5 minutes to 120 hours whereupon the compound (VI) can be obtained.

Examples of the trialkylsilyl halide or the triarylsilyl halide are trimethylsilyl chloride, trimethylsilyl bromide, trimethylsilyl iodide, triethylsilyl chloride, dimethylethylsilyl chloride and triphenylsilyl chloride.

Examples of the halogenated salt are lithium bromide, sodium bromide, potassium bromide, lithium chloride, sodium chloride, potassium chloride, lithium iodide, sodium iodide and potassium iodide.

Examples of the reducing agent are 1,1,3,3-tetramethyldisiloxane, triethylsilane, sodium borohydride, sodium cyanoborohydride, sodium triacetoxyborohydride and lithium aluminum hydride.

Examples of the halogenating agent are hydrochloric acid, hydrogen bromide, hydrogen iodide, thionyl chloride, phosphorus oxychloride and phosphorus tribromide.

Examples of the base are triethylamine, N,N-diisopropylethylamine, 1,8-diazabicyclo[5.4.0]-7-undecene (hereinafter, abbreviated as DBU), potassium carbonate and sodium hydride.

Examples of the alkylsulfonyl chloride or arylsulfonyl chloride are methanesulfonyl chloride, p-toluenesulfonyl chloride and benzenesulfonyl chloride.

Examples of the metal cyanide are sodium cyanide, potassium cyanide and copper cyanide.

Examples of the inert solvent are tetrahydrofuran (hereinafter, abbreviated as THF), dioxane, 1,2-dimethoxyethane, diethyl ether, acetonitrile, dimethylformamide (hereinafter, abbreviated as DMF), dimethyl sulfoxide (hereinafter, abbreviated as DMSO), methanol, ethanol, propanol, dichloromethane, chloroform, benzene, toluene, pyridine and ethyl acetate.

Process 2

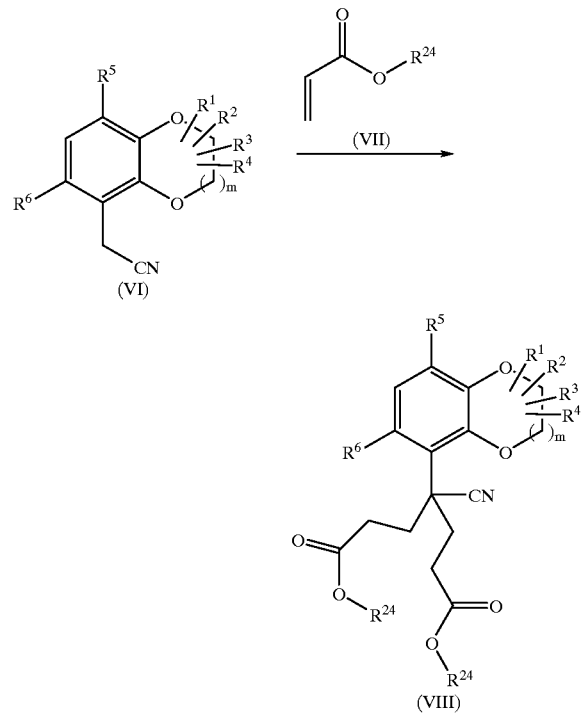

(In the formulae, m, $R^1$, $R^2$, $R^3$, $R^4$, $R^5$ and $R^6$ have the same meanings as defined above and $R^{24}$ stands for the lower alkyl having the same meaning as defined above.)

The compound (VIII) can be obtained by the following method.

The compound (VI) is treated with the compound (VII) in an inert solvent in the presence of a catalytic amount to a large excess amount of a base at the temperature between 0° C. and the boiling point of the used solvent for 5 minutes to 48 hours whereby the compound (VIII) can be obtained.

Examples of the base are benzyltrimethylammonium hydroxide (Triton B), sodium hydroxide, potassium hydroxide, sodium hydride, potassium hydride, sodium methoxide, lithium diisopropylamide (hereinafter, abbreviated as LDA), pyridine, potassium tert-butoxide, DBU, triethylamine and diisopropylethylamine.

Examples of the inert solvent are THF, dioxane, diethyl ether, methanol, ethanol, 1-propanol, 2-propanol, n-butanol, tert-butyl alcohol, pyridine, acetonitrile, DMF, DMSO, 1,2-dimethoxyethane, diethylene glycol methyl ether, dichloromethane, chloroform, benzene and toluene.

Process 3

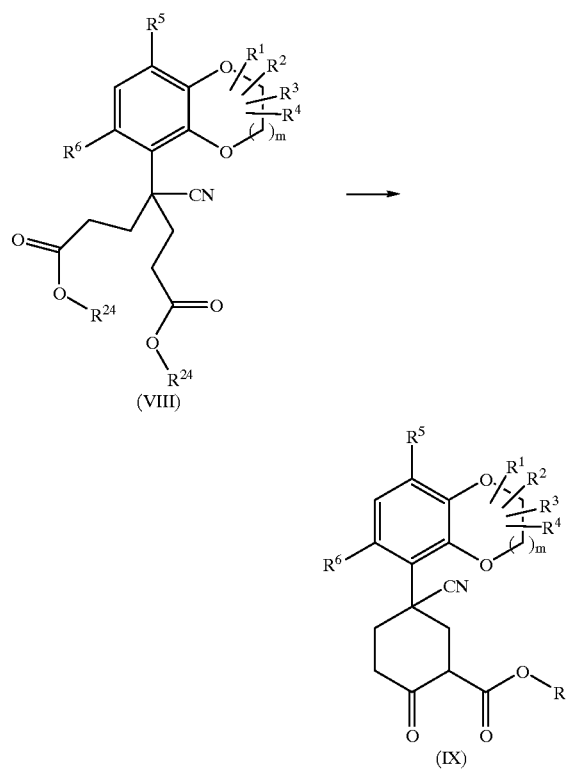

(In the formulae, m, $R^1$, $R^2$, $R^3$, $R^4$, $R^5$, $R^6$ and $R^{24}$ have the same meanings as defined above.)

The compound (IX) can be obtained by the following method from the compound (VIII).

The compound (VIII) is treated in an inert solvent in the presence of one equivalent to a large excess of a base at the temperature between 0° C. and the boiling point of the used solvent for 5 minutes to 48 hours whereupon the compound (IX) can be obtained.

Examples of the base are sodium hydride, potassium hydride, sodium hydroxide, potassium hydroxide, sodium methoxide, sodium ethoxide, LDA, pyridine, potassium tert-butoxide, DBU, triethylamine and diisopropylethylamine.

Examples of the inert solvent are THF, dioxane, pyridine, diethyl ether, methanol, ethanol, 1-propanol, 2-propanol, 1-butanol, tert-butyl alcohol, acetonitrile, DMF, DMSO, 1,2-dimethoxyethane, diethylene glycol methyl ether, dichloromethane, chloroform, benzene and toluene.

Process 4

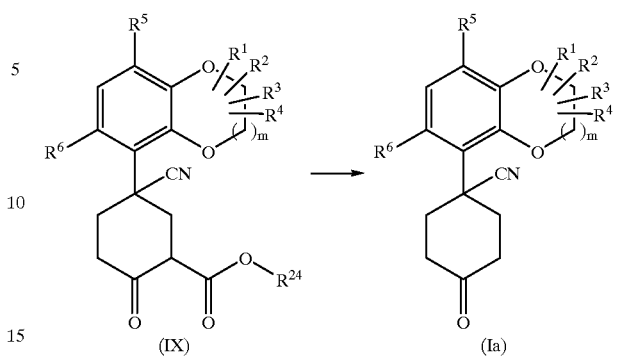

(In the formulae, m, $R^1$, $R^2$, $R^3$, $R^4$, $R^5$, $R^6$ and $R^{24}$ have the same meanings as defined above.)

The compound (Ia) can be obtained according to the following reaction step.

The compound (IX) is treated in an inert solvent in the presence of one equivalent to a large excess of water at the temperature between 60° C. and the boiling point of the used solvent for 5 minutes to 120 hours whereupon the compound (Ia) can be obtained. If necessary, a catalytic amount to an excess amount of a salt such as sodium chloride, lithium chloride, sodium iodide, lithium iodide or sodium cyanide may be added thereto.

Examples of the inert solvent are dioxane, toluene, DMF, DMSO, tert-butyl alcohol, acetonitrile, 1,2-dimethoxyethane, diethylene glycol methyl ether, ethylene glycol, triethylene glycol and water.

Process 5

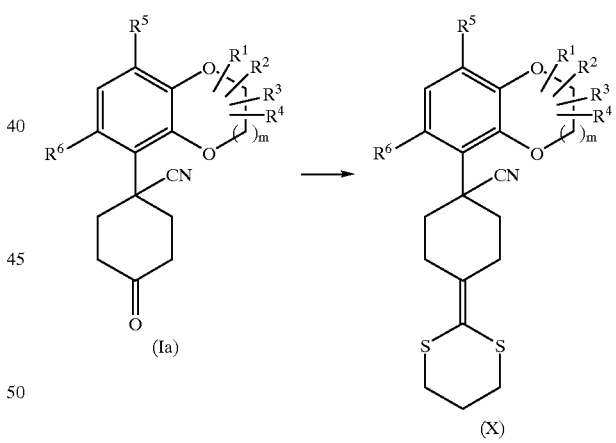

(In the formulae, m, $R^1$, $R^2$, $R^3$, $R^4$, $R^5$ and $R^6$ have the same meanings as defined above.)

The compound (X) can be obtained according to the following reaction step.

2-Trimethylsilyl-1,3-dithiane is treated with a base in an inert solvent at the temperature between −100° C. and 0° C., followed by reaction with the compound (Ia) at the temperature between −100° C. and 30° C. for 1 minute to 12 hours whereupon the compound (X) can be obtained.

Examples of the base are sodium hydride, potassium hydride, sodium hydroxide, potassium hydroxide, sodium methoxide, butyl lithium, LDA, lithium bistrimethylsilylamide, sodium bistrimethylsilylamide, potassium bistrimethylsilylamide, potassium tert-butoxide, DBU, triethylamine, diisopropylethylamine and ethyl magnesium bromide.

Examples of the inert solvent are THF, dioxane, diethyl ether, 1,2-dimethoxyethane and diisopropyl ether.

Process 6

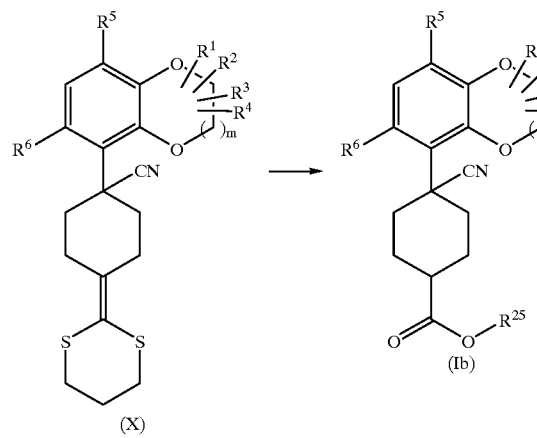

(In the formulae, m, $R^1$, $R^2$, $R^3$, $R^4$, $R^5$ and $R^6$ have the same meanings as defined above and $R^{25}$ represents the same lower alkyl as defined above.)

The compound (Ib) can be obtained according to the following reaction step.

The compound (X) is treated in a solvent [with regard to the said solvent, a lower alcohol which will be mentioned later may be used solely or as a mixed solvent containing the lower alcohol (dioxane/lower alcohol, THF/lower alcohol, and the like); and the said lower alcohol also acts as a reagent for esterifying the carboxyl group which is obtained by the reaction] in the presence of one equivalent to an excess amount of a divalent mercury salt and an acid at the temperature between 0° C. and the boiling point of the used solvent for 5 minutes to 48 hours whereupon the compound (Ib) can be obtained.

Examples of the divalent mercury salt are mercury chloride ($HgCl_2$) and mercury acetate [$Hg(OCOCH_3)_2$]. Examples of the acid are perchloric acid, sulfuric acid, hydrochloric acid, trifluoroacetic acid, p-toluenesulfonic acid, methanesulfonic acid and boron trifluoride.

Examples of the solvent are lower alcohols (methanol, ethanol, 1-propanol, 2-propanol, 1-butanol, 2-methyl-1-propanol, 2-butanol, tert-butyl alcohol, 1-pentanol, 1-hexanol, 1-heptanol, 1-octanol, and the like), a mixed solvent of dioxane/a lower alcohol (wherein the lower alcohol has the same meaning as defined above) and a mixed solvent of THF/a lower alcohol (wherein the lower alcohol has the same meaning as defined above).

Process 7

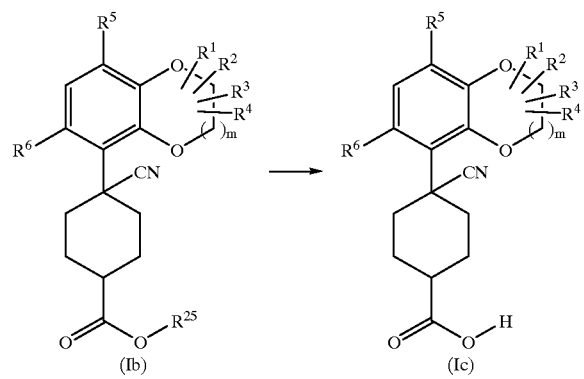

(In the formulae, m, $R^1$, $R^2$, $R^3$, $R^4$, $R^5$, $R^6$ and $R^{25}$ have the same meanings as defined above.)

The compound (Ic) can be obtained according to the following reaction step.

The compound (Ib) is treated with an aqueous solution of an alkali in an inert solvent at the temperature between 0° C. and the boiling point of the used solvent for 5 minutes to 48 hours whereupon the compound (Ic) can be obtained.

Examples of the aqueous solution of an alkali are aqueous solutions of sodium hydroxide, potassium hydroxide and lithium hydroxide while examples of the inert solvent are ethanol, dioxane, methanol, THF, a mixed solvent of ethanol/THF, a mixed solvent of methanol/THF, and DMSO.

Process 8

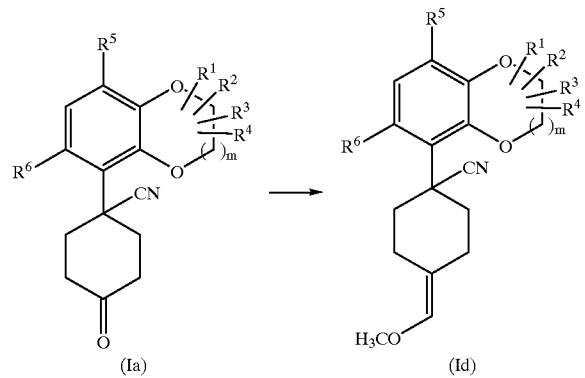

(In the formulae, m, $R^1$, $R^2$, $R^3$, $R^4$, $R^5$ and $R^6$ have the same meanings as defined above.)

The compound (Id) can be obtained according to the following reaction step.

One equivalent to an excess amount of methoxymethyl-triphenylphosphonium chloride is treated with one equivalent to an excess amount of a base in an inert solvent at the temperature between −100° C. and the boiling point of the used solvent, followed by reaction with the compound (Ia) at the temperature between −100° C. and the boiling point of the used solvent for 5 minutes to 12 hours whereupon the compound (Id) can be obtained.

Examples of the base are sodium hydride, potassium hydride, sodium hydroxide, potassium hydroxide, sodium methoxide, butyl lithium, LDA, lithium bistrimethylsilylamide, sodium bistrimethylsilylamide, potassium bistrimethylsilylamide, potassium tert-butoxide, DBU, sodium amide and sodium ethoxide.

Examples of the inert solvent are THF, dioxane, diethyl ether, 1,2-dimethoxyethane, DMF and diisopropyl ether.

Process 9

(In the formulae, m, $R^1$, $R^2$, $R^3$, $R^4$, $R^5$ and $R^6$ have the same meanings as defined above.)

The compound (Ie) can be obtained according to the following reaction step.

The compound (Id) is treated with a catalytic amount to an excess amount of an acid in the absence of a solvent or in an inert solvent at the temperature between 0° C. and the boiling point of the used solvent for 5 minutes to 48 hours whereupon the compound (Ie) can be obtained.

Examples of the acid are hydrochloric acid, sulfuric acid, acetic acid, trifluoroacetic acid, p-toluenesulfonic acid, methanesulfonic acid, 10-camphorsulfonic acid, boron trifluoride and aluminum chloride.

Examples of the inert solvent are THF, acetone, acetonitrile, methanol, ethanol, dioxane and a mixed solvent of such an inert solvent with water.

Process 10

(In the formulae, m, $R^1$, $R^2$, $R^3$, $R^4$, $R^5$ and $R^6$ have the same meanings as defined above.)

The compound (If) can be obtained according to the following reaction step.

The compound (Ia) is treated with one equivalent to a large excess of trimethylsulfoxonium iodide or trimethylsulfonium iodide in the presence of one equivalent to a large excess of a base in an inert solvent at the temperature between −30° C. and the boiling point of the used solvent for 5 minutes to 48 hours whereupon the compound (If) can be obtained.

Examples of the base are sodium hydride, potassium hydride, sodium hydroxide, potassium hydroxide, sodium methoxide, butyl lithium, LDA, lithium bistrimethylsilylamide, sodium bistrimethylsilylamide, potassium bistrimethylsilylamide, potassium tert-butoxide, DBU, sodium amide and sodium ethoxide.

Examples of the inert solvent are THF, dioxane, diethyl ether, 1,2-dimethoxyethane, DMF and diisopropyl ether.

Process 11

(In the formulae, m, $R^1$, $R^2$, $R^3$, $R^4$, $R^5$ and $R^6$ have the same meanings as defined above.)

The compound (Ie) can be obtained according to the following reaction step.

The compound (If) is treated with one equivalent to an excess amount of an acid in the absence of a solvent or in an inert solvent at the temperature between 0° C. and the boiling point of the used solvent for 5 minutes to 48 hours whereupon the compound (Ie) can be obtained.

Examples of the acid are hydrochloric acid, sulfuric acid, hydrogen bromide, magnesium chloride, magnesium bromide, lithium bromide, trifluoroacetic acid, lithium perchlorate, p-toluenesulfonic acid, methanesulfonic acid, 10-camphorsulfonic acid, boron trifluoride, aluminum chloride and silica gel.

Examples of the inert solvent are THF, acetone, acetonitrile, methanol, ethanol and dioxane.

Process 12

(In the formulae, m, $R^1$, $R^2$, $R^3$, $R^4$, $R^5$ and $R^6$ have the same meanings as defined above.)

The compound (Ic) can be obtained according to the following reaction step.

The compound (Ie) is treated with one equivalent to an excess amount of an oxidizing agent in an inert solvent at the temperature between 0° C. and the boiling point of the used solvent for 5 minutes to 48 hours whereupon the compound (Ic) can be obtained.

Examples of the oxidizing agent are sodium chlorite, potassium permanganate and hydrogen peroxide.

When sodium chlorite is used as an oxidizing agent, one equivalent to an excess amount of 2-methyl-2-butene, sulfamic acid, DMSO, an aqueous solution of hydrogen peroxide, or the like may be added if necessary, or further, one equivalent to an excess amount of sodium dihydrogen phophate may be added thereto.

Examples of the inert solvent are tert-butyl alcohol, acetic acid, DMSO, acetone and acetonitrile.

Process 13

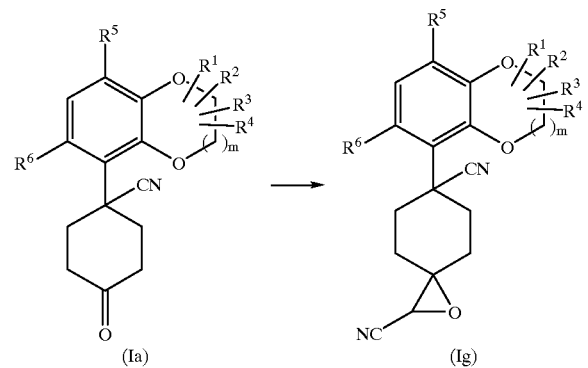

(In the formulae, m, $R^1$, $R^2$, $R^3$, $R^4$, $R^5$ and $R^6$ have the same meanings as defined above.)

The compound (Ig) can be obtained according to the following reaction step.

The compound (Ia) is treated with one equivalent to a large excess of chloroacetonitrile in the presence of one equivalent to a large excess of a base in an inert solvent at the temperature between −10° C. and the boiling point of the used solvent for 5 minutes to 48 hours whereupon the compound (Ig) can be obtained. If necessary, a catalytic amount to an excess amount of a salt such as benzyltriethylammonium chloride, benzyltriethylammonium bromide, benzyltrimethylammonium chloride, benzyltrimethylammonium bromide, tetrabutylammonium chloride, tetrabutylammonium bromide, tetraethylammonium chloride or triethylmethylammonium bromide may be added thereto.

Examples of the base are potassium carbonate, sodium carbonate, sodium hydride, potassium hydride, lithium hydroxide, sodium hydroxide, potassium hydroxide, calcium hydroxide, sodium methoxide, butyl lithium, potassium tert-butoxide, DBU and sodium ethoxide.

Examples of the inert solvent are methanol, ethanol, 1-propanol, 2-propanol, tert-butyl alcohol, ethyl acetate, toluene, THF, 1,2-dimethoxyethane, DMF, DMSO and diisopropyl ether.

Process 14

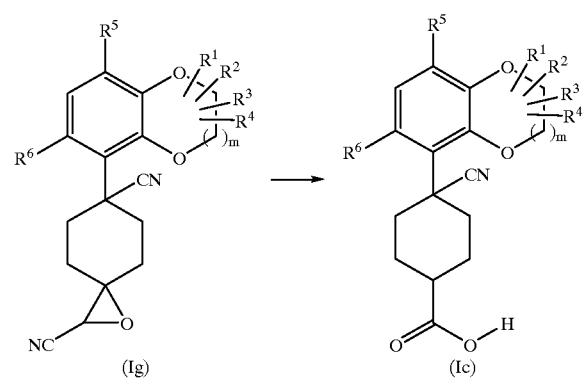

(In the formulae, m, $R^1$, $R^2$, $R^3$, $R^4$, $R^5$ and $R^6$ have the same meanings as defined above.)

The compound (Ic) can be obtained according to the following reaction step.

The compound (Ig) is treated with one equivalent to an excess amount of magnesium bromide or lithium bromide in the absence of a solvent or in an inert solvent in the presence of one equivalent to an excess amount of water at the temperature between 0° C. and the boiling point of the used solvent for 5 minutes to 48 hours whereupon the compound (Ic) can be obtained.

Examples of the inert solvent are THF, DMF, acetone, acetonitrile, methanol, ethanol, dioxane and a mixed solvent of DMF/acetonitrile.

Process 15

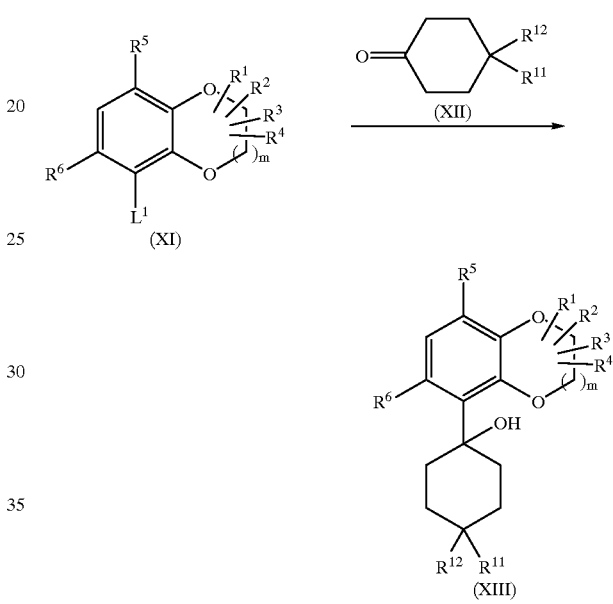

(In the formulae, m, $R^1$, $R^2$, $R^3$, $R^4$, $R^5$, $R^6$, $R^{11}$ and $R^{12}$ each have the same meanings as defined above and $L^1$ represents chlorine, bromine or iodine.)

The compound (XIII) can be obtained according to the following reaction step.

The starting compound (XI) can be obtained according to a known method (WO 98/22455) or a method similar thereto. A commercially available compound can be used as the compound (XII).

The compound (XI) is treated with one equivalent to an excess amount of a base in an inert solvent at the temperature between −100° C. and room temperature for 5 minutes to 10 hours, followed by reaction with one equivalent to an excess amount of the compound (XII) at the temperature between −100° C. and room temperature for 5 minutes to 30 hours whereupon the compound (XIII) can be obtained. If necessary, tetramethylethylenediamine, cerium chloride, or the like may be added thereto.

Examples of the base are lithium, magnesium, methyl lithium, methyl magnesium bromide, ethyl magnesium bromide and butyl lithium.

Examples of the inert solvent are THF, dioxane, diethyl ether, 1, 2-dimethoxyethane, diethylene glycol dimethyl ether, benzene, toluene and hexane.

Process 16

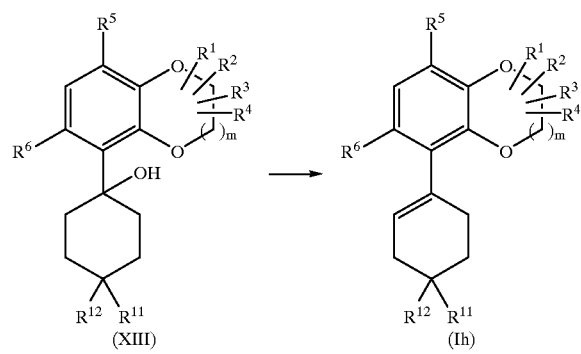

(In the formulae, m, $R^1$, $R^2$, $R^3$, $R^4$, $R^5$, $R^6$, $R^{11}$ and $R^{12}$ have the same meanings as defined above.)

The compound (Ih) can be obtained according to the following reaction step.

The compound (XIII) is treated with one equivalent to an excess amount of an acid in the absence of a solvent or in an inert solvent at the temperature between 0° C. and the boiling point of the used solvent for 5 minutes to 48 hours whereupon the compound (Ih) can be obtained. If necessary, water may be added thereto.

Examples of the acid are hydrochloric acid, sulfuric acid, 10-camphorsulfonic acid, acetic acid, formic acid, trifluoroacetic acid, p-toluenesulfonic acid, methanesulfonic acid, boron trifluoride and aluminum chloride.

Examples of the inert solvent are THF, acetone, acetonitrile, toluene, xylene, methanol, ethanol, 1-propanol, 2-propanol, 1-butanol, 2-butanol, tert-butyl alcohol, 1-pentanol, 1-hexanol, 1-heptanol, 1-octanol and dioxane.

Process 17

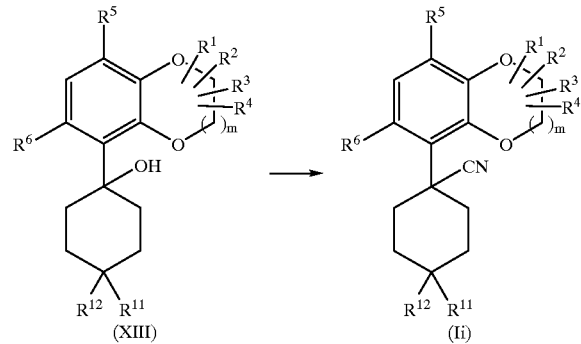

(In the formulae, m, $R^1$, $R^2$, $R^3$, $R^4$, $R^5$, $R^6$, $R^{11}$ and $R^{12}$ have the same meanings as defined above.)

The compound (Ii) can be obtained according to the following reaction step.

The compound (XIII) is treated with one equivalent to an excess amount of a cyanide in the presence of one equivalent to an excess amount of an acid in an inert solvent at the temperature between −100° C. and the boiling point of the used solvent for 5 minutes to 48 hours whereupon the compound (Ii) can be obtained.

Examples of the acid are hydrochloric acid, sulfuric acid, 10-camphorsulfonic acid, acetic acid, formic acid, trifluoroacetic acid, p-toluenesulfonic acid, methanesulfonic acid, titanium tetrachloride, boron trifluoride and aluminum chloride.

Examples of the cyanide are trimethylsilyl cyanide, sodium cyanide and potassium cyanide.

Examples of the inert solvent are THF, dioxane, diethyl ether, 1,2-dimethoxyethane, methanol, ethanol, acetonitrile, dichloromethane, 1, 2-dichloroethane, chloroform and toluene.

Process 18

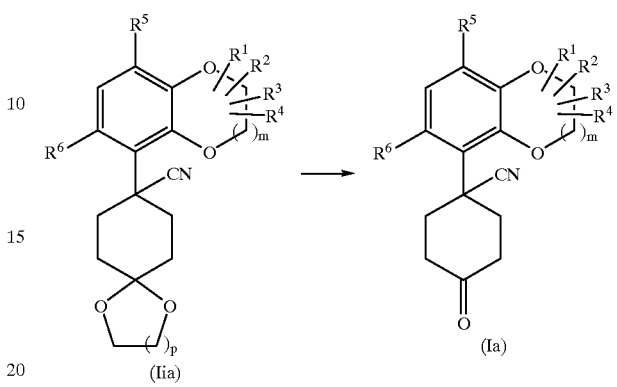

(In the formulae, m, p, $R^1$, $R^2$, $R^3$, $R^4$, $R^5$ and $R^6$ have the same meanings as defined above.)

The compound (Ia) can be obtained according to the following reaction step.

The starting compound (Iia) can be synthesized in such a manner that a compound (XIII) wherein $R^{11}$ and $R^{12}$ have a ketal structure is obtained using a compound (XII) wherein $R^{11}$ and $R^{12}$ have a ketal structure as a starting material in Process 15 and a method mentioned in Process 17 is applied using the compound (XIII) wherein $R^{11}$ and $R^{12}$ have a ketal structure as a starting material.

The compound (Iia) is treated with one equivalent to an excess amount of an acid in the absence of a solvent or in an inert solvent at the temperature between 0° C. and the boiling point of the used solvent for 5 minutes to 48 hours whereupon the compound (Ia) can be obtained.

Examples of the acid are hydrochloric acid, sulfuric acid, 10-camphorsulfonic acid, acetic acid, formic acid, trifluoroacetic acid, p-toluenesulfonic acid, methanesulfonic acid, boron trifluoride and aluminum chloride.

Examples of the inert solvent are THF, acetone, acetonitrile, toluene, methanol, ethanol, 1-propanol, 2-propanol, 1-butanol, 2-butanol, tert-butyl alcohol, 1-pentanol, 1-hexanol, 1-heptanol, 1-octanol, dioxane and a mixed solvent of such an insert solvent with water.

Process 19

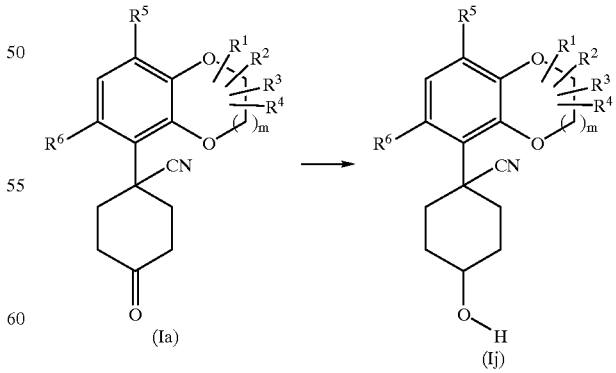

(In the formulae, m, $R^1$, $R^2$, $R^3$, $R^4$, $R^5$ and $R^6$ have the same meanings as defined above.)

The compound (Ij) can be obtained according to the following reaction step.

The compound (Ia) is treated with one equivalent to an excess amount of a reducing agent in an inert solvent at the temperature between −100° C. and the boiling point of the used solvent for 5 minutes to 48 hours whereupon the compound (Ij) can be obtained.

Examples of the reducing agent are 1,1,3,3-tetramethyldisiloxane, triethylsilane, sodium borohydride, sodium cyanoborohydride, sodium triacetoxyborohydride and lithium aluminum hydride.

Examples of the inert solvent are methanol, ethanol, 1-propanol, 2-propanol, 1-butanol, 2-butanol, tert-butyl alcohol, 1-pentanol, 1-hexanol, 1-heptanol, 1-octanol and dioxane.

Process 20

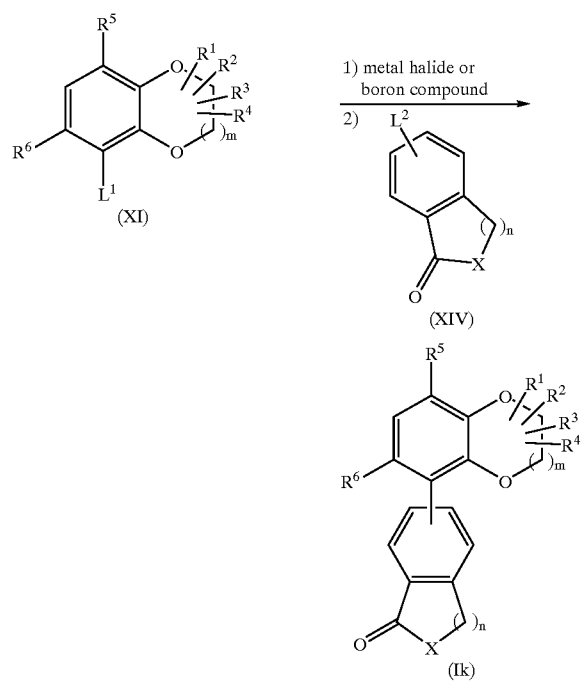

(In the formulae, m, n, $R^1$, $R^2$, $R^3$, $R^4$, $R^5$, $R^6$, $L^1$ and X each have the same meanings as defined above, and $L^2$ represents chlorine, bromine, iodine or a trifluoromethanesulfonate group.)

The compound (Ik) can be obtained according to the following reaction step.

With regard to the compound (XIV), the commercially available one may be used or it may be obtained according to a known method [Tetrahedron Lett., 30, 5499 (1992)].

After the compound (XI) is treated with a base in an inert solvent at the temperature between −100° C. and room temperature for 5 minutes to 10 hours, the resulting compound is treated with a metal halide or a boron compound at the temperature between −100° C. and the boiling point of the used solvent for 5 minutes to 30 hours, followed by further reaction with the compound (XIV) in an inert solvent in the presence of a catalytic amount to an excess amount of a palladium complex at the temperature between room temperature and the boiling point of the used solvent for 5 minutes to 30 hours whereupon the compound (Ik) can be obtained. Incidentally, in the above reaction which is carried out in the presence of a catalytic amount to an excess amount of a palladium complex, a salt such as lithium chloride or silver oxide may be added, if necessary.

Examples of the base are lithium, magnesium, methyl lithium, methyl magnesium bromide, ethyl magnesium bromide and butyl lithium.

Examples of the metal halide are halogenated alkyl tin derivatives such as chlorotributyltin and chlorotrimethyltin and halogenated zinc derivatives such as zinc chloride, zinc bromide and zinc iodide while examples of the boron compound are trimethyl borate, triisopropyl borate, tributyl borate, triethyl borate and borane.

Examples of the palladium complex are tetrakis(triphenylphosphine)palladium, dichlorobis(triphenylphosphine)palladium, dichlorobis(acetonitrile)palladium, [1,1'-bis(diphenylphosphino)ferrocene]dichloropalladium and palladium acetate.

Examples of the inert solvent used in the reaction with a metal halide or a boron compound are THF, dioxane, diethyl ether, 1,2-dimethoxyethane, diethylene glycol dimethyl ether, benzene, toluene and hexane.

Examples of the inert solvent used in the reaction in the presence of a palladium complex are THF, dioxane, diethyl ether, ethylene glycol, triethylene glycol, 1,2-dimethoxyethane, diethylene glycol dimethyl ether, methanol, ethanol, 1-butanol, 2-propanol, dichloromethane, chloroform, acetonitrile, benzene, toluene, dimethylacetamide, DMF and DMSO.

Process 21

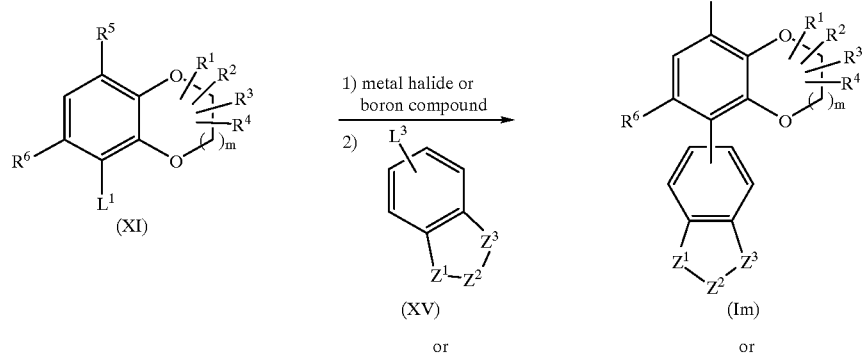

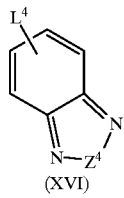

(XVI)

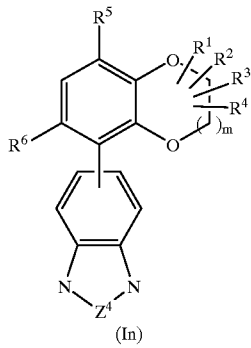

(In)

(In the formulae, m, $R^1$, $R^2$, $R^3$, $R^4$, $R^5$, $R^6$, $L^1$ and $Z^1$—$Z^2$—$Z^3$ each have the same meanings as defined above, $Z^4$ represents an oxygen atom or a sulfur atom, and $L^3$ and $L^4$ represent chlorine, bromine, iodine or a trifluoromethanesulfoxy group.)

The compound (Im) and the compound (In) can be obtained according to the following reaction step.

With regard to the compound (XV) and the compound (XVI), the commercially available ones may be used or they may be obtained according to known methods [J. Chem. Soc., Perkin Trans. 1, 1954 (1973); J. Org. Chem., 60(7), 1936 (1995); Tetrahedron Lett., 30(42), 7719 (1994); Chem. Pharm. Bull., 40(10), 2597 (1992); J. Heterocyclic Chem., 7, 815 (1970); J. Chem. Soc. Chem. Comm., 1183 (1985); etc.]

The compound (XI) is treated with a base in an inert solvent at the temperature between −100° C. and room temperature for 5 minutes to 10 hours, followed by reaction with a metal halide or a boron compound at the temperature between −100° C. and the boiling point of the used solvent for 5 minutes to 30 hours. The resulting compound is treated with the compound (XV) in an inert solvent in the presence of a catalytic amount to an excess amount of a palladium complex or a nickel complex at the temperature between room temperature and the boiling point of the used solvent for 5 minutes to 30 hours whereby the compound (Im) can be obtained. Incidentally, when the compound (XVI) is used instead of the compound (XV) and the same reaction as in the case of the compound (XV) is carried out, the compound (In) is obtained.

In the above-mentioned reaction carried out in the presence of a catalytic amount to an excess amount of a palladium complex or a nickel complex, a salt such as lithium chloride or silver oxide may be added thereto, if necessary.

Examples of the base are lithium, magnesium, methyl lithium, methyl magnesium bromide, ethyl magnesium bromide and butyl lithium.

Examples of the metal halide are halogenated alkyl tin derivatives such as chlorotributyltin and chlorotrimethyltin and halogenated zinc derivatives such as zinc chloride, zinc bromide and zinc iodide while examples of the boron compound are trimethyl borate, triisopropyl borate, tributyl borate, triethyl borate and borane.

Examples of the palladium complex are tetrakis(triphenylphosphine)palladium, dichlorobis(triphenylphosphine)palladium, dichlorobis(acetonitrile)palladium, [1,1'-bis(diphenylphosphino)ferrocene]dichloropalladium and palladium acetate.

Examples of the nickel complex are [1,1'-bis(diphenylphosphino)ferrocene]dichloronickel and dichlorobis(triphenylphosphine)nickel.

Examples of the inert solvent used in the reaction with a metal halide or a boron compound are THF, dioxane, diethyl ether, 1,2-dimethoxyethane, diethylene glycol dimethyl ether, benzene, toluene and hexane.

Examples of the inert solvent used in the reaction in the presence of a palladium complex or a nickel catalyst are THF, dioxane, diethyl ether, ethylene glycol, triethylene glycol, 1,2-dimethoxyethane, diethylene glycol dimethyl ether, methanol, ethanol, 1-butanol, 2-propanol, dichloromethane, chloroform, acetonitrile, benzene, toluene, dimethylacetamide, DMF and DMSO.

The compound (Ima) which is the compound (Im) wherein $Z^1$—$Z^2$—$Z^3$ is C(=O)—NH—C(=O) can also be obtained in such a way that a reaction similar to that mentioned in Process 21 is carried out using the compound (XI) and a diethyl 4-halogenated phthalate such as diethyl 4-bromophthalate followed by hydrolysis and the product obtained thereby is treated with urea.

The compound (I) wherein $R^9$ is carbamoyl can be obtained using the compound (I) wherein $R^9$ is cyano according to a known method ["Jikken Kagaku Koza (Handbook of Experimental Chemistry)", fourth edition, edited by the Chemical Society of Japan, 22, 151–154 (1992)] or a method similar thereto.

The compound (I) wherein $R^9$ is cyano is converted to the compound wherein the moiety corresponding to $R^9$ is an aldehyde according to a known method ["Jikken Kagaku Koza (Handbook of Experimental Chemistry)", fourth edition, edited by the Chemical Society of Japan, 21, 89–94 (1992)] or a method similarly thereto, and then the compound (I) wherein $R^9$ is ethynyl can be obtained according to a known method ["Jikken Kagaku Koza (Handbook of Experimental Chemistry)", fourth edition, edited by the Chemical Society of Japan, 19, 306–307 (1992)] or a method similar thereto.

The intermediates and the desired compounds in each of the above-mentioned process can be isolated and purified by separation and purification methods conventionally used in synthetic organic chemistry such as filtration, extraction, washing, drying, concentration, recrystallization and various kinds of chromatography. The intermediates may be subjected to the subsequent reaction without particular purification.

When it is desired to obtain a salt of the compound (I), the compound (I) is dissolved or suspended in a suitable solvent, then an acid or a base is added thereto, and the resulting salt may be isolated and purified.

Further, the compound (I) and pharmaceutically acceptable salts thereof can also exist in the form of adducts with water or various solvents, which are also within the scope of the present invention.

Specific examples of the compound (I) obtained according to the present invention are shown in Table 1.
TABLE 1
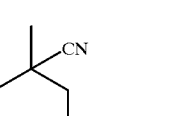
| Compd. No. | W | R | m |
|---|---|---|---|
| 1 | 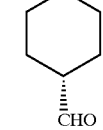 | H | 1 |
| 2 | 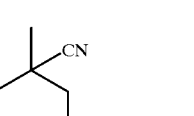 | H | 1 |
| 3 | 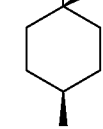 | H | 1 |
| 4 | 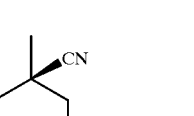 | H | 1 |
| 5 | 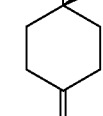 | H | 1 |
| 6 | 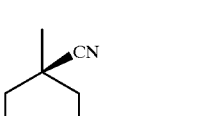 | H | 1 |
| 7 | 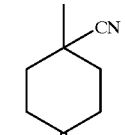 | H | 1 |
| 8 | 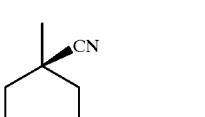 | H | 1 |
| 9 | 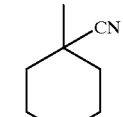 | H | 1 |
| 10 | 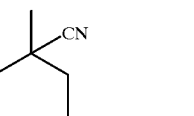 | H | 1 |
| 11 | 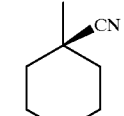 | H | 1 |
| 12 |  | $CH_3$ | 0 |
| 13 |  | $CH_3$ | 0 |

TABLE 1-continued

| 14 | [structure: 1-methyl-4-(methoxycarbonyl)cyclohexane-1-carbonitrile] | CH₃ | 0 |
| 15 | [structure: 1-methyl-4-carboxycyclohexane-1-carbonitrile] | CH₃ | 0 |
| 16 | [structure: 4-methylcyclohex-3-enone] | H | 1 |
| 17 | [structure: 5-methyl-2,3-dihydro-1H-inden-1-one] | H | 1 |
| 18 | [structure: 6-methyl-3,4-dihydronaphthalen-1(2H)-one] | H | 1 |
| 19 | [structure: methyl-benzosuberone] | H | 1 |
| 20 | [structure: 1-methyl-4-(ethoxycarbonylmethyl)cyclohexane-1-carbonitrile] | H | 1 |
| 21 | [structure: 1-methyl-4-(carboxymethyl)cyclohexane-1-carbonitrile] | H | 1 |
| 22 | [structure: 5-methylisobenzofuran-1(3H)-one] | H | 1 |
| 23 | [structure: 5-methylisoindoline-1,3-dione] | H | 1 |
| 24 | [structure: 1-methyl-4-(ethoxycarbonyl)cyclohexane-1-carbonitrile] | H | 2 |
| 25 | [structure: 1-methyl-4-carboxycyclohexane-1-carbonitrile] | H | 2 |
| 26 | [structure: 1-methyl-4-(ethoxycarbonyl)cyclohexane-1-carbonitrile, cis] | H | 0 |
| 27 | [structure: 1-methyl-4-carboxycyclohexane-1-carbonitrile, cis] | H | 0 |

TABLE 1-continued

[Structure: benzodioxane with R⁵ at top position, R,R substituents on carbon adjacent to O, (CH₂)ₘ bridge, W at bottom position]

| Compd. No. | W | R | m | R⁵ |
|---|---|---|---|---|
| 28 | 1-CN,4-COOH-cyclohexyl | H | 1 | OH |
| 29 | 1-CN,4-COOCH₂CH₃-cyclohexyl | H | 1 | OH |
| 30 | 1-CN,4-COOCH₂CH₃-cyclohexyl | H | 1 | OCHF₂ |
| 31 | 1-CN,4-COOH-cyclohexyl | H | 1 | OCHF₂ |
| 32 | 1-CN,4-COOH-cyclohexyl | H | 0 | OH |
| 33 | 1-CN,4-COOCH₂CH₃-cyclohexyl | H | 0 | OH |
| 34 | 1-CN,4-COOCH₂CH₃-cyclohexyl | H | 0 | OCHF₂ |
| 35 | 1-CN,4-COOH-cyclohexyl | H | 0 | OCHF₂ |
| 36 | 1-CN,4-COOH-cyclohexyl | H | 2 | OH |
| 37 | 1-CN,4-COOCH₂CH₃-cyclohexyl | H | 2 | OH |
| 38 | 1-CN,4-COOCH₂CH₃-cyclohexyl | H | 2 | OCHF₂ |
| 39 | 1-CN,4-COOH-cyclohexyl | H | 2 | OCHF₂ |
| 40 | 1-CN,4-COOCH₂CH₃-cyclohexyl | CH₃ | 0 | OCH₃ |

TABLE 1-continued

| | | | | |
|---|---|---|---|---|
| 41 | (cyclohexane with CN up, COOH down) | $CH_3$ | 0 | $OCH_3$ |
| 42 | (cyclohexane with CN up, $COOCH_2CH_3$ down) | $-(CH_2)_4-$ | 0 | $OCH_3$ |
| 43 | (cyclohexane with CN up, COOH down) | $-(CH_2)_4-$ | 0 | $OCH_3$ |
| 44 | (cyclohexane with CN up, COOH down) | $CH_3$ | 0 | OH |
| 45 | (cyclohexane with CN up, $COOCH_2CH_3$ down) | $CH_3$ | 0 | OH |
| 46 | (cyclohexane with CN up, $COOCH_2CH_3$ down) | $CH_3$ | 0 | $OCHF_2$ |
| 47 | (cyclohexane with CN up, COOH down) | $CH_3$ | 0 | $OCHF_2$ |
| 48 | (cyclohexane with CN up, COOH down) | $-(CH_2)_4-$ | 0 | OH |
| 49 | (cyclohexane with CN up, $COOCH_2CH_3$ down) | $-(CH_2)_4-$ | 0 | OH |
| 50 | (cyclohexane with CN up, $COOCH_2CH_3$ down) | $-(CH_2)_4-$ | 0 | $OCHF_2$ |
| 51 | (cyclohexane with CN up, COOH down) | $-(CH_2)_4-$ | 0 | $OCHF_2$ |
| 52 | (cyclohexane with CN up, COOH down) | $CH_3$ | 1 | $OCH_3$ |
| 53 | (cyclohexane with CN up, $COOCH_2CH_3$ down) | $CH_3$ | 1 | $OCH_3$ |
| 54 | (cyclohexane with CN up, COOH down) | $CH_3$ | 1 | OH |

TABLE 1-continued

| No. | Structure | R | n | X |
|---|---|---|---|---|
| 55 | cyclohexane with CN and COOCH$_2$CH$_3$ substituents | CH$_3$ | 1 | OH |
| 56 | cyclohexane with CN and COOCH$_2$CH$_3$ substituents | CH$_3$ | 1 | OCHF$_2$ |
| 57 | cyclohexane with CN and COOH substituents | CH$_3$ | 1 | OCHF$_2$ |

The pharmacological activities of the representative compounds (I) are described in more detail by Test Examples.

Test Example 1

Inhibition Test on Recombinant Human PDE IV Enzyme

Human phosphodiesterase cDNA (HSPDE4A) was isolated from testicles. Its predicted amino acid sequence is identical with the sequence (HSPDE4A5) reported by Bolger, G. et al. (Mol. Cell. Biol., 6558 (1993)) except that 223 amino acids have been deleted from the N-terminal thereof. This recombinant protein was expressed by an E. coli expression plasmid and then purified. The PDE activity was measured in the following 2-step process according to the method of Kincaid, R. and Manganiello, V. [Method. Enzymol., 159, 457 (1988)]. The substrate used was [$^3$H] cAMP (final concentration: 1 μmol/L), and the reaction was performed in a standard mixture containing N,N-bis(2-hydroxyethyl)-2-aminoethanesulfonic acid (50 mmol/L, pH 7.2), MgCl$_2$ (1 mmol/L) and soybean trypsin inhibitor (0.1 mg/ml). The reaction was initiated by adding the enzyme thereto, and the mixture was incubated at 30° C. for 10 to 30 minutes. The reaction was quenched by hydrochloric acid, and the formed 5'-AMP was completely decomposed with 5'-nucleosidase. This sample was subjected to chromatography on DEAE-Sephadex A-25, and the eluted [$^3$H] adenosine was counted 15 with a scintillation counter. The test compound was added after dissolved (concentration: 1.7%) in DMSO.

In this study, Compound 5 showed enzyme inhibitory activity of over 87% at a drug concentration of 1 mol/L.

Although the compound (I) or pharmaceutically acceptable salts thereof can also be administered as such, it is usually desirable to provide them in the form of various pharmaceutical preparations. Such pharmaceutical preparations may be used for animals and humans.

The pharmaceutical preparations according to the present invention may contain the compound (I) or a pharmaceutically acceptable salt thereof as an active ingredient, alone or as a mixture with other therapeutically effective components. Further, such pharmaceutical preparations are obtained by any means which are well-known in the technical field of pharmaceutics after mixing the active ingredient with one or more pharmaceutically acceptable carriers.

Examples of the effective ingredient to be mixed therewith are a serotonin (5HT)$_3$ receptor antagonist, a serotonin (5HT)$_4$ receptor agonist, a serotonin (5HT)$_{1A}$ receptor agonist, a dopamine (D)$_2$ receptor antagonist, a histamine (H)$_1$ receptor antagonist, a muscarine receptor antagonist, a neurokinin (NK)$_1$ receptor antagonist and an endothelin (ET)$_A$ receptor antagonist.

It is desired to use the administration route which is the most effective in therapy such as oral administration and parenteral administration which includes intrabuccal, intratracheal, intrarectal, subcutaneous, intramuscular and intravenous administration.

The administration form includes sprays, capsules, tablets, granules, syrups, emulsions, suppositories, injections, ointments and tapes.

Liquid preparations such as emulsions and syrups which are suitable for oral administration can be obtained using water, sugars such as sucrose, sorbitol and fructose, glycols such as polyethylene glycol and propylene glycol, oils such as sesame oil, olive oil and soybean oil, preservatives such as p-hydroxybenzoate and flavors such as strawberry flavor and peppermint. Capsules, tablets, powder and granules can be obtained using excipients such as lactose, glucose, sucrose and mannitol, disintegrators such as starch and sodium alginate, lubricants such as magnesium stearate and talc, binders such as polyvinyl alcohol, hydroxypropyl cellulose and gelatin, surfactants such as fatty acid esters, and plasticizers such as glycerin.

Preparations suitable for parenteral administration comprise a sterilized aqueous agent containing the active compound, which is preferably isotonic to the blood of a patient. For example, a solution for injection is prepared using a carrier such as a salt solution, a glucose solution or a mixture of a saline solution and a glucose solution. Preparations for intrarectal administration are prepared using a carrier such as cacao fat, hydrogenated fat and hydrogenated carboxylic acid, and provided as suppositories. Sprays are prepared using an active compound itself or an active compound with a carrier which can disperse the active compound as fine particles to facilitate absorption without stimulating oral or respiratory mucosa. Examples of such carriers are lactose and glycerin. Preparations such as aerosol and dry powder can be used depending on the properties of the active compound and carriers used.

These parenteral preparations may also contain one or more auxiliary components selected from diluents, flavors, preservatives, excipients, disintegrators, lubricants, binders, surfactants, and plasticizers, all of which are mentioned in the above oral preparations.

The effective dose and administration schedule of the compound (I) or a pharmaceutically acceptable salt thereof may vary depending on the form of administration, the age and body weight of a patient, and the type or degree of the disease to be treated, but usually, in the case of oral administration, the compound (I) or a pharmaceutically acceptable salt thereof is administered in a dose of 0.01 mg to 1 g/adult/day, preferably 0.05 to 50 mg/adult/day, at one time or in several parts. In the case of parenteral administration such as intravenous administration, the compound (I) or a pharmaceutically acceptable salt thereof is administered in a dose of 0.001 to 100 mg/adult/day, preferably 0.01 to 10 mg/adult/day, at one time or in several parts. However, these doses vary depending on the various conditions described above.

Hereinafter, the mode of the present invention is described by Examples.

DESCRIPTION OF THE PREFERRED EMBODIMENTS

Example 1

4-Cyano-4-(8-methoxy-1,4-benzodioxan-5-yl) cyclohexanone (Compound 1)

(Step A) Synthesis of 2-(8-methoxy-1,4-benzodioxan-5-yl) acetonitrile (Compound 1a)

To a solution of 8-methoxy-1,4-benzodioxane-5-carbaldehyde (12 g, 62 mmol) in acetonitrile (140 mL) was added lithium bromide (12 g, 110 mmol), and then trimethylsilyl chloride (12 mL, 95 mmol) was added dropwise. After 15 minutes, the mixture was ice-cooled, and 1,1,3,3-tetramethyldisiloxane (19 mL, 110 mmol) was added dropwise, followed by stirring at room temperature for 2 hours. The mixture was diluted with dichloromethane, and then was filtered through Celite. The solvent was evaporated in vacuo to give a pale yellow oil. To a solution of the obtained crude 5-bromomethyl-8-methoxy-1,4-benzodioxane in DMF(180 mL) was added sodium cyanide (9.2 g, 190 mmol), followed by stirring at room temperature for 60 hours. To the mixture was added water under ice-cooling, and the precipitated solid was collected by filtration to give Compound 1a (6.8 g, 53%) as an ash-colored solid.

Melting Point: 121–125° C.

$^1$H-NMR (CDCl$_3$, δ, ppm) 3.60 (s, 2H), 3.88 (s, 3H), 4.33 (s, 4H), 6.50 (d, J=8 Hz, 1H), 6.86 (d, J=8 Hz, 1H).

MASS (m/z) 205 (M$^+$).

(Step B) Synthesis of dimethyl 4-cyano-4-(8-methoxy-1,4-benzodioxan-5-yl)pimelate (Compound 1b)

To a solution of Compound 1a (6.2 g, 30 mmol) obtained in Step A in acetonitrile (94 mL) were added a 40% methanolic solution of Triton B (1.4 mL, 3.0 mmol) and methyl acrylate (27 mL, 300 mmol), followed by refluxing for 5 hours. The mixture was allowed to cool, and then poured into water, followed by extraction with ethyl acetate. The organic layer as washed with brine and dried over sodium sulfate, and the solvent was evaporated in vacuo. The residue was purified by silica gel column chromatography (eluted with hexane/ethyl acetate=2/1) to give Compound 1b (6.4 g, 56%) as a pale yellow oil.

$^1$H-NMR (CDCl$_3$, δ, ppm) 2.05–2.37 (m, 4H), 2.39–2.59 (m, 2H), 2.62–2.82 (m, 2H), 3.60 (s, 6H), 3.87 (s, 3H), 4.20–4.40 (m, 4H), 6.48 (d, J=9 Hz, 1H), 7.01 (d, J=9 Hz, 1H).

MASS (m/z) 377 (M$^+$).

(Step C) Synthesis of 4-cyano-4-(8-methoxy-1,4-benzodioxan-5-yl)-2-methoxycarbonylcyclohexanone (Compound 1c)

To a solution of Compound 1b (6.4 g, 17 mmol) obtained in Step B in 1,2-dimethoxyethane (96 mL) was added 60% sodium hydride (2.0 g, 50 mmol). After refluxing for 3 hours, the mixture was allowed to cool, poured into ice water, acidified with 6 mol/L hydrochloric acid and extracted with ethyl acetate. The organic layer was washed with brine and dried over sodium sulfate, and the solvent was evaporated. The residue was purified by silica gel column chromatography (eluted with hexane/ethyl acetate= 2/1) to give Compound 1c (5.0 g, 86%) as a white solid.

Melting Point: 129–132° C.

$^1$H-NMR (CDCl$_3$, δ, ppm) 2.21–2.50 (m, 3H), 2.61–2.89 (m, 2H), 3.11(d, J=15 Hz, 1H), 3.79 (s, 3H), 3.89 (s, 3H), 4.37 (s, 4H), 6.49 (d, J=9 Hz, 1H), 6.84 (d, J=9 Hz, 1H), 12.2 (s, 1H).

MASS (m/z) 345 (M$^+$).

(Step D) Synthesis of Compound 1

A mixture of Compound 1c (5.0 g, 15 mmol) obtained in Step C, DMSO(50 mL), water (5 mL), and sodium chloride (5.0 g) was stirred at 150° C. for 5 hours. The mixture was allowed to cool, and added water, followed by extraction with ethyl acetate. The organic layer was washed with brine and dried over sodium sulfate, and the solvent was evaporated in vacuo. The residue was purified by silica gel column chromatography (eluted with hexane/ethyl acetate=3/1) to give Compound 1 (3.6 g, 86%) as a white solid.

Melting Point: 157–161° C.

$^1$H-NMR (CDCl$_3$, δ, ppm) 2.21–2.41 (m, 2H), 2.45–2.72 (m, 4H), 2.81–3.00 (m, 2H), 3.89 (s, 3H), 4.37 (s, 4H), 6.51 (d, J=9 Hz, 1H), 6.88 (d, J=9 Hz, 1H).

MASS (m/z) 287 (M$^+$).

Example 2

4-Cyano-4-(8-methoxy-1,4-benzodioxan-5-yl) cyclohexanone ethyleneketal (Compound 2)

(Step A) Synthesis of 4-hydroxy-4-(8-methoxy-1,4-benzodioxan-5-yl)cyclohexanone ethyleneketal (Compound 2a)

To a solution of 5-bromo-8-methoxy-1,4-benzodioxane (10 g, 41 mmol) in THF (65 mL) was added dropwise a 1.59 mol/L solution of n-butyl lithium in hexane (28 mL, 45 mmol) at −78° C. After 15 minutes, a solution of 1,4-cyclohexadione monoethyleneketal (9.6 g, 61 mmol) in THF (50 mL) was added dropwise. The mixture was stirred for 1 hour, followed by stirring at room temperature for 20 minutes. Water was added and the mixture was extracted with ethyl acetate. The extract was washed with brine and dried over sodium sulfate. The solvent was evaporated, and the residue was purified by silica gel column chromatography (eluted with hexane/ethyl acetate=1/1) to give Compound 2a (9.0 g, 68%) as a white solid.

Melting Point: 94–96° C.

$^1$H-NMR (CDCl$_3$, δ, ppm) 1.58–1.72 (m, 2H), 1.88–2.28 (m, 6H), 3.57 (s, 1H), 3.86 (s, 3H), 3.90–4.07 (m, 4H), 4.35 (s, 4H), 6.46 (d, J=9 Hz, 1H), 6.82 (d, J=9 Hz, 1H).

MASS (m/z) 322 (M$^+$).

(Step B) Synthesis of Compound 2

To a solution of Compound 2a (0.49 g, 1.5 mmol) obtained in Step A in dichloromethane (4.9 mL), trimethylsilyl cyanide (0.26 mL, 1.9 mmol) was added at −78° C., then boron trifluoride-ethyl ether complex (0.20 mL, 1.6 mmol) was added dropwise, and the mixture was stirred for 10 minutes, followed by stirring at room temperature for 10 minutes. A saturated aqueous solution of sodium bicarbonate was added and the mixture was extracted with ethyl acetate. The extract was washed with brine and dried over sodium sulfate, and the solvent was evaporated. The residue was purified by silica gel column chromatography (eluted with hexane/ethyl acetate=2/1) to give Compound 2 (0.30 g, 61%) as a colorless oil.

$^1$H-NMR (CDCl$_3$, δ, ppm) 1.79–1.95 (m, 2H), 2.06–2.20 (m, 4H), 2.30–2.46 (m, 2H), 3.87 (s, 3H), 3.90–4.07 (m, 4H), 4.36 (s, 4H), 6.48 (d, J=9 Hz, 1H), 6.82 (d, J=9 Hz, 1H).

MASS (m/z) 331 (M$^+$).

Example 3

Compound 1

To a solution of Compound 2 (0.29 g, 0.87 mmol) obtained in Example 2 in acetone (2.9 mL), 6 mol/L hydrochloric acid (1.2 mL, 7.2 mmol) was added, and the mixture was refluxed for 3 hours. The mixture was allowed to cool and poured into a saturated aqueous solution of sodium bicarbonate, the mixture was extracted with ethyl acetate, and the extract was washed with brine. The mixture was dried over sodium sulfate, and the solvent was evaporated to give Compound 1 (0.23 g, 92%) as a white solid.

Example 4

Methyl cis-4-cyano-4-(8-methoxy-1,4-benzodioxan-5-yl)cyclohexanecarboxylate (Compound 3) and methyl trans-4-cyano-4-(8-methoxy-1,4-benzodioxan-5-yl)cyclohexanecarboxylate (Compound 4)

(Step A) Synthesis of 2-[4-cyano-4-(8-methoxy-1,4-benzodioxan-5-yl)cyclohexylidene]-1,3-dithiane (Compound 3a)

To a solution of 2-trimethylsilyl-1,3-dithiane (5.0 mL, 26 mmol) in THF (50 mL) was added dropwise a 1.54 mol/L solution of n-butyl lithium in hexane (17 mL, 26 mmol) under ice-cooling. After 10 minutes, the mixture was cooled to −78° C., and a solution of Compound 1 (3.6 g, 13 mmol) obtained in Example 1 in THF (40 mL) was added dropwise. After 10 minutes, brine was added to the mixture, followed by addition of water at room temperature. The mixture was extracted with ethyl acetate, the extract was dried over sodium sulfate, and the solvent was evaporated. The residue was purified by silica gel column chromatography (eluted with hexane/ethyl acetate=4/1) to give Compound 3a (3.9 g, 79%) as a white solid.

Melting Point: 164–166° C.

$^1$H-NMR (CDCl$_3$, δ, ppm) 1.70–1.92 (m, 2H), 2.05–2.24 (m, 2H), 2.28–2.53 (m, 4H), 2.89 (t, J=6 Hz, 4H), 3.18–3.38 (m, 2H), 3.87 (s, 3H), 4.36 (s, 4H), 6.47 (d, J=9 Hz, 1H), 6.79 (d, J=9 Hz, 1H).

MASS (m/z) 389 (M$^+$).

(Step B) Synthesis of Compound 3 and Compound 4

To a suspension of Compound 3a (3.9 g, 10 mmol) obtained in Step A in methanol (120 mL), 70% perchloric acid (1.7 mL, 20 mmol), and mercury chloride (HgCl$_2$) (4.3 g, 16 mmol) were added, and the mixture was stirred for 4 hours. The mixture was diluted with dichloromethane and was filtered through Celite, the filtrate was poured into a saturated aqueous solution of sodium bicarbonate, and the mixture was extracted with dichloromethane. The organic layer was washed with brine and dried over sodium sulfate and the solvent was evaporated. The residue was purified by silica gel column chromatography (eluted with hexane/ethyl acetate=1/1) to give the crude Compound 3 as a white solid and also to give Compound 4 (0.18 g, 5.5%) as a colorless oil. Compound 3 was further recrystallized from ethyl acetate to give white crystals (0.57 g, 17%).

Compound 3

Melting Point: 123–124° C.

$^1$H-NMR (CDCl$_3$, δ, ppm) 1.75–2.22 (m, 6H), 2.27–2.51 (m, 3H), 3.71 (s, 3H), 3.88 (s, 3H), 4.36 (s, 4H), 6.48 (d, J=9 Hz, 1H), 6.84 (d, J=9 Hz, 1H).

MASS (m/z) 331 (M$^+$).

Compound 4

$^1$H-NMR (CDCl$_3$, δ, ppm) 1.92–2.38 (m, 8H), 2.70–2.88 (m, 1H), 3.69 (s, 3H), 3.87 (s, 3H), 4.36 (s, 4H), 6.48 (d, J=9 Hz, 1H), 6.81 (d, J=9 Hz, 1H).

MASS (m/z) 331 (M$^+$).

Example 5 cis-4-Cyano-4-(8-methoxy-1,4-benzodioxan-5-yl) cyclohexanecarboxylic acid (Compound 5)

To a solution of Compound 3 (0.55 g, 1.7 mmol) obtained in Example 4 in methanol (3.3 mL) and THF (3.3 mL) was added dropwise a 1.3 mol/L aqueous solution of potassium hydroxide (2.6 mL), followed by stirring at room temperature for 1 hour. The mixture was poured into water, ethyl acetate was added, and an aqueous layer was extracted. The aqueous layer was acidified with 1 mol/L hydrochloric acid, and the precipitated solid was collected by filtration and re-slurried with ethanol to give of Compound 5 (0.45 g, 86%) as a white solid.

Melting Point: 228–230° C.

$^1$H-NMR (DMSO-d$_6$, δ, ppm) 1.59–1.90 (m, 4H), 1.94–2.10 (m, 2H), 2.20–2.45 (m, 3H), 3.75 (s, 3H), 4.27 (dd, J=5, 12 Hz, 4H), 6.60 (d, J=9 Hz, 1H), 6.79 (d, J=9 Hz, 1H), 12.2 (br s, 1H).

MASS (m/z) 317 (M$^+$).

Elemental analysis: C$_{17}$H$_{19}$NO$_5$ Found (%) C, 64.09; H, 6.01; N, 4.51. Calcd. (%) C, 64.34; H, 6.03; N, 4.41.

Example 6

1-(8-Methoxy-1,4-benzodioxan-5-yl)-4-methoxymethylenecyclohexane carbonitrile (Compound 6)

To a suspension of (methoxymethyl) triphenylphosphonium chloride (34 g, 99 mmol) in THF (320 mL) was added potassium tert-butoxide (11 g, 99 mmol). The mixture was stirred at room temperature for 15 minutes, and a solution of Compound 1 (15 g, 52 mmol) obtained in Example 1 in THF (150 mL) was added dropwise, followed by stirring at room temperature for 45 minutes. Water was added to the reaction mixture and the mixture was extracted with ethyl acetate. The organic layer was washed with brine and dried over sodium sulfate. The solvent was evaporated in vacuo, and the residue was purified by silica gel column chromatography (eluted with hexane/ethyl acetate=3/1) to give Compound 6 (14 g, 82%) as a white solid.

Melting Point: 112–113° C.

$^1$H-NMR (CDCl$_3$, δ, ppm) 1.67–1.82 (m, 2H), 2.08–2.60 (m, 5H), 2.82–2.98 (m, 1H), 3.57 (s, 3H), 3.87 (s, 3H), 4.36 (s, 4H), 5.84 (s, 1H), 6.47 (d, J=9 Hz, 1H), 6.80 (d, J=9 Hz, 1H).

MASS (m/z) 315 (M$^+$).

Example 7 cis-4-Cyano-4-(8-methoxy-1,4-benzodioxan-5-yl) cyclohexane carbaldehyde (Compound 7) and trans-4-cyano-4-(8-methoxy-1,4-benzodioxan-5-yl) cyclohexane carbaldehyde (Compound 8)

To a solution of Compound 6 (10 g, 32 mmol) obtained in Example 6 in acetone (100 mL) was added dropwise 6 mol/L hydrochloric acid (210 mL), and the mixture was stirred at room temperature for 2 hours, neutralized by adding a 5 mol/L aqueous solution of sodium hydroxide and extracted with ethyl acetate. The organic layer was washed with a saturated aqueous solution of sodium bicarbonate and then with brine. The mixture was dried over magnesium sulfate, the solvent was evaporated in vacuo, and the residue was purified by silica gel column chromatography (eluted with hexane/ethyl acetate=2/1) to give Compound 7 (7.7 g, 80%) and Compound 8 (1.7 g, 18%) each being as a colorless oil.

Compound 7

$^1$H-NMR (CDCl$_3$, δ, ppm) 1.80–2.35 (m, 7H), 2.38–2.57 (m, 2H), 3.88 (s, 3H), 4.36 (s, 4H), 6.49 (d, J=9 Hz, 1H), 6.85 (d, J=9 Hz, 1H), 9.68 (s, 1H).

MASS (m/z) 301 (M$^+$).

Compound 8

$^1$H-NMR (CDCl$_3$, δ, ppm) 1.75–1.96 (m, 2H), 2.06–2.37 (m, 6H), 2.56–2.65 (m, 1H), 3.87 (s, 3H), 4.33 (s, 4H), 6.46 (d, J=9 Hz, 1H), 6.78 (d, J=9 Hz, 1H), 9.73 (s, 1H).

MASS (m/z) 301 (M$^+$).

Example 8 cis-4-Cyano-4-(8-methoxy-1,4-benzodioxan-5-yl) cyclohexanecarboxylic acid (Compound 5)

To a solution of Compound 7 (7.7 g, 26 mmol) obtained in Example 7, sodium dihydrogen phosphate (3.1 g, 26 mmol) and 2-methyl-2-butene (12 mL, 120 mmol) in tert-butyl alcohol (155 mL) was added dropwise 46 mL of a aqueous solution of 80% sodium chlorite (3.2 g, 28 mmol) under ice-cooling, and the mixture was stirred at room temperature for 1 hour. To the mixture was added sodium hydrogen sulfite (5.3 g, 51 mmol), followed by stirring for 15 minutes, a 2 mol/L aqueous solution of sodium hydroxide was added, and the resulting mixture was washed with ethyl acetate. The mixture was adjusted to pH 3.5 with 6 mol/L hydrochloric acid, and the precipitated solid was collected by filtration and recrystallized from ethanol to give Compound 5 (5.5 g, 67%) as white crystals.

Example 9 cis-4-Cyano-4-(8-methoxy-1,4-benzodioxan-5-yl) cyclohexanol (Compound 9)

To a solution of Compound 1 (0.42 g, 1.5 mmol) obtained in Example 1 in methanol (8.4 mL) was added sodium borohydride (0.11 g, 3.0 mmol) under ice-cooling. The mixture was stirred at room temperature for 1 hour, sodium borohydride (0.057 g, 1.5 mmol) was added again under ice-cooling, followed by stirring at room temperature for 30 minutes, 1 mol/L hydrochloric acid was added thereto under ice-cooling, and the mixture was extracted with ethyl acetate. The organic layer was washed with brine and dried over sodium sulfate, and the solvent was evaporated in vacuo. The residue was purified by silica gel column chromatography (eluted with hexane/ethyl acetate=1/2), followed by recrystallization from ethanol to give Compound 9 (0.20 g, 48%) as white crystals.

Melting Point: 137–138° C.

$^1$H-NMR (CDCl$_3$, δ, ppm) 1.75–1.99 (m, 4H), 2.01–2.22 (m, 2H), 2.30–2.54 (m, 2H), 3.56–3.79 (m, 1H), 3.87 (s, 3H), 4.38 (s, 4H), 6.48 (d, J=8 Hz, 1H), 6.83 (d, J=8 Hz, 1H).

MASS (m/z) 289 (M$^+$).

Elemental analysis: C$_{16}$H$_{19}$NO$_4$.0.1H$_2$O Found (%) C, 66.21; H, 6.94; N, 4.82. Calcd. (%) C, 66.01; H, 6.65; N. 4.81.

Example 10

Ethyl 4-cyano-4-(8-methoxy-1,4-benzodioxan-5-yl) cyclohexanylideneacetate (Compound 10)

To a solution of triethyl phosphonoacetate (0.72 mL, 3.6 mmol) in THF (9.4 mL) was added 60% sodium hydride (0.15 g, 3.6 mmol) under ice-cooling. The mixture was stirred at room temperature for 15 minutes, Compound 1 (0.94 g, 3.3 mmol) obtained in Example 1 was added under ice-cooling, and the mixture was stirred at room temperature for 30 minutes. Then, water was added under ice-cooling, the mixture was extracted with ethyl acetate, and the organic layer was washed with brine and dried over sodium sulfate. The solvent was evaporated in vacuo, and the residue was purified by silica gel column chromatography (eluted with hexane/ethyl acetate=2/1) to give Compound 10 (1.4 g, 97%) as a white solid.

Melting Point: 110–112° C.

$^1$H-NMR (CDCl$_3$, δ, ppm) 1.28 (t, J=7 Hz, 3H), 1.85–2.10 (m, 2H), 2.31–2.60(m, 4H), 2.67–2.89 (m, 1H), 3.87 (s, 3H), 3.92–4.12 (m, 1H), 4.16 (q, J=7 Hz, 2H), 4.36 (s, 4H), 5.71 (s, 1H), 6.48 (d, J=9 Hz, 1H), 6.81 (d, J=9 Hz, 1H).

MASS (m/z) 357 (M$^+$).

Example 11

4-Cyano-4-(8-methoxy-1,4-benzodioxan-5-yl) cyclohexanylideneacetic acid (Compound 11)

To a suspension of Compound 10 (0.31 g, 0.87 mmol) obtained in Example 10 in ethanol (3.1 mL) and THF (3.1 mL) was added a 2 mol/L aqueous solution of sodium hydroxide (0.65 mL, 1.3 mmol), the mixture was stirred at 70° C. for 1 hour, and then a 2 mol/L aqueous solution of sodium hydroxide (0.65 mL, 1.3 mmol) was further added, followed by stirring at 70° C. for 1 hour. 1 mol/L hydrochloric acid was added dropwise under ice-cooling, and the mixture was extracted with ethyl acetate. The organic layer was washed with brine and dried over sodium sulfate, the solvent was evaporated in vacuo, and the residue was triturated with ethanol to give Compound 11 (0.23 g, 82%) as a white solid.

Melting Point: 203–204 ° C.

$^1$H-NMR (DMSO-d$_6$, δ, ppm) 1.75–2.00 (m, 2H), 2.05–2.67 (m, 5H), 3.74 (s, 3H), 3.80–4.00 (m, 1H), 4.15–4.43 (m, 4H), 5.69 (s, 1H), 6.59 (d, J=9 Hz, 1H), 6.81 (d, J=9 Hz, 1H), 12.1 (br s, 1H).

MASS (m/z) 329 (M$^+$).

Elemental analysis: C$_{18}$H$_{19}$NO$_5$.0.1H$_2$O Found (%) C, 65.30; H, 6.09; N, 4.19. Calcd. (%) C, 65.29; H, 5.84; N, 4.23.

Example 12

4-Cyano-4-(2,2-dimethyl-7-methoxy-1,3-benzodioxol-4-yl)cyclohexanone (Compound 12)

(Step A) Synthesis of 2-(2,2-dimethyl-7-methoxy-1,3-benzodioxol-4-yl)acetonitrile (Compound 12a)

To a solution of 2,2-dimethyl-7-methoxy-1,3-benzodioxole-4-carbaldehyde (9.3 g, 45 mmol) obtained by the method mentioned in the Japanese Published Unexamined Patent Application No. 98/147585 and by a method similar thereto in acetonitrile (47 mL) was added lithium bromide (8.9 g, 85 mmol), and then trimethylsilyl chloride (8.5 mL, 67 mmol) was added dropwise. After 15 minutes, the mixture was ice-cooled, and 1,1,3,3-tetramethyldisiloxane (13 mL, 76 mmol) was added dropwise, followed by stirring at room temperature for 2 hours. The resulting mixture was diluted with toluene and filtered through Celite. The solvent was evaporated in vacuo from the filtrate to give a pale yellow oil. To a solution of this crude 7-bromomethyl-2,2-dimethyl-4-methoxy-1,3-benzodioxole in DMF (73 mL) was added sodium cyanide (5.0 g, 102 mmol), and the mixture was stirred at room temperature for18 hours. Under ice-cooling, water was added, and the mixture was extracted with ethyl acetate. The organic layer was washed with brine and dried over sodium sulfate, and the solvent was evaporated in vacuo. The residue was purified by silica gel column chromatography (eluted with hexane/ethyl acetate=5/1) to give Compound 12a (9.1 g, 92%) as an ash-colored solid.

Melting Point: 58–59° C.

$^1$H-NMR (CDCl$_3$, δ, ppm) 1.71 (s, 6H), 3.60 (s, 2H), 3.88 (s, 3H), 6.50 (d, J=9 Hz, 1H), 6.76 (d, J=9 Hz, 1H).

MASS (m/z) 219 (M$^+$).

(Step B) Synthesis of dimethyl 4-cyano-4-(2,2-dimethyl-7-methoxy-1,3-benzodioxol-4-yl)pimelate (Compound 12b)

To a solution of Compound 12a (9.0 g, 41 mmol) obtained in Step A in acetonitrile (135 mL) were added a 40% methanolic solution of Triton B (1.9 mL, 4.1 mmol) and methyl acrylate (37 mL, 410 mmol), and the mixture was stirred at room temperature for 30 minutes. Water and 1 mol/L hydrochloric acid were added, followed by extraction with ethyl acetate. The organic layer was washed with brine and dried over sodium sulfate, and the solvent was evaporated in vacuo. The residue was purified by silica gel column chromatography (eluted with hexane/ethyl acetate=5/2) to give Compound 12b (11 g, 68%) as a pale yellow oil.

$^1$H-NMR (CDCl$_3$, δ, ppm) 1.69 (s, 6H), 2.05–2.31 (m, 4H), 2.40–2.64 (m, 4H), 3.60 (s, 6H), 3.89 (s, 3H), 6.49 (d, J=9 Hz, 1H), 6.88 (d, J=9 Hz, 1H).

MASS (m/z) 391 (M$^+$).

(Step C) Synthesis of 4-cyano-4-(2,2-dimethyl-7-methoxy-1,3-benzodioxol-4-yl)-2-methoxycarbonylcyclohexanone (Compound 12c)

To a solution of Compound 12b (11 g, 27 mmol) obtained in Step B in 1,2-dimethoxyethane (161 mL) was added 60% sodium hydride (3.3 g, 83 mmol). After refluxing for 3 hours, the mixture was allowed to cool and poured into ice water, and the mixture was acidified with 6 mol/L hydrochloric acid and extracted with ethyl acetate. The organic layer was washed with brine and dried over sodium sulfate, and the solvent was evaporated. The residue was purified by silica gel column chromatography (eluted with hexane/ethyl acetate=3/1) to give Compound 12c (8.4 g, 86%) as a white solid.

Melting Point: 146–147° C.

$^1$H-NMR (CDCl$_3$, δ, ppm) 1.71 (s, 3H), 1.73 (s, 3H), 2.12–2.27 (m, 1H), 2.32–2.55 (m, 2H), 2.67–3.00 (m, 3H), 3.78 (s, 3H), 3.89 (s, 3H), 6.51 (d, J=9 Hz, 1H), 6.92 (d, J=9 Hz, 1H), 12.2 (s, 1H).

MASS (m/z) 359 (M$^+$).

(Step D) Synthesis of Compound 12

A mixture of Compound 12c (8.3 g, 23 mmol) obtained in the step C, DMSO (83 mL), water (8.3 mL) and sodium chloride (8.3 g) was stirred at 150° C. for 12 hours. The mixture was allowed to cool, and water was added, followed by extraction with ethyl acetate. The organic layer was washed with brine and dried over sodium sulfate, and the solvent was evaporated. The residue was purified by silica gel column chromatography (eluted with hexane/ethyl acetate=3/1) to give Compound 12 (5.6 g, 81%) as a white solid.

Melting Point: 153–154° C.

$^1$H-NMR (CDCl$_3$, δ, ppm) 1.72 (s, 6H), 2.35–2.61 (m, 6H), 2.77–2.97 (m, 2H), 3.90 (s, 3H), 6.53 (d, J=9 Hz, 1H), 6.97 (d, J=9 Hz, 1H).

MASS (m/z) 301 (M$^+$).

Example 13

Methyl cis-4-cyano-4-(2,2-dimethyl-7-methoxy-1,3-benzodioxol-4-yl)cyclohexanecarboxylate (Compound 13) and trans-4-cyano-4-(2,2-dimethyl-7-methoxy-1,3-benzodioxol-4-yl) cyclohexanecarboxylate (Compound 14)

(Step A) Synthesis of 2-[4-cyano-4-(2,2-dimethyl-7-methoxy-1,3-benzodioxol-4-yl)cyclohexylidene]-1,3-dithiane (Compound 13a)

To a solution of 2-trimethylsilyl-1,3-dithiane (0.56 mL, 3.0 mmol) in THF (5.6 mL) was added dropwise a solution of 1.54 mol/L of n-butyl lithium in hexane (1.9 mL, 3.0 mmol) under ice-cooling. After 15 minutes, the mixture was cooled to –78° C., and a solution of Compound 12 (0.42 g, 1.4 mmol) obtained in Example 12 in THF (0.6 mL) was added dropwise. After 20 minutes, brine was added and then water was added at room temperature. The mixture was extracted with ethyl acetate, the extract was dried over sodium sulfate, and the solvent was evaporated. The residue was purified by silica gel column chromatography (eluted with hexane/ethyl acetate=6/1) to give Compound 13a (0.53 g, 93%) as a white solid.

Melting Point: 194–197° C.

$^1$H-NMR (CDCl$_3$, δ, ppm) 1.72 (s, 6H), 1.86–2.53 (m, 8H), 2.90 (t, J=6 Hz, 4H), 3.17–3.33 (m, 2H), 3.88 (s, 3H), 6.48 (d, J=9 Hz, 1H), 6.86 (d, J=9 Hz, 1H).

MASS (m/z) 403 (M$^+$).

(Step B) Synthesis of Compound 13 and Compound 14

To a suspension of Compound 13a (3.0 g, 7.4 mmol) obtained in Step A in methanol (105 mL) were added 70% perchloric acid (1.3 mL, 15 mmol) and mercury chloride (HgCl$_2$)(3.2 g, 12 mmol), and the mixture was stirred at 60° C. for 1 hour. The mixture was diluted with dichloromethane and filtered through Celite, and the filtrate was poured into a saturated aqueous solution of sodium bicarbonate, followed by extraction with dichloromethane. The organic layer was washed with brine and dried over sodium sulfate, and the solvent was evaporated. The residue was purified by silica gel column chromatography (eluted with hexane/ethyl acetate=3/1) to give Compound 13 (1.4 g, 53%) as a white solid and Compound 14 (0.31 g, 12%) as a colorless oil.

Compound 13

Melting Point: 79–80° C.

$^1$H-NMR (CDCl$_3$, δ, ppm) 1.72 (s, 6H), 1.87–2.27 (m, 8H), 2.30–2.43 (m, 1H), 3.71 (s, 3H), 3.88 (s, 3H), 6.49 (d, J=9 Hz, 1H), 6.92 (d, J=9 Hz, 1H).

MASS (m/z) 345 (M$^+$).

Compound 14

$^1$H-NMR (CDCl$_3$, δ, ppm) 1.71 (s, 6H), 1.90–2.26 (m, 8H), 2.72–2.80 (m, 1H), 3.70 (s, 3H), 3.88 (s, 3H), 6.48 (d, J=9 Hz, 1H), 6.83 (d, J=9 Hz, 1H).

MASS (m/z) 345 (M$^+$).

Example 14 cis-4-Cyano-4-(2,2-dimethyl-7-methoxy-1,3-benzodioxol-4-yl)cyclohexanecarboxylic acid (Compound 15)

To a mixture of Compound 13 (1.7 g, 5.0 mmol) obtained in Example 13 and methanol (10 mL) was dissolved in THF (5.2 mL). To the mixture was added dropwise a 1.3 mol/L aqueous solution of potassium hydroxide (7.7 mL, 10 mmol), followed by stirring at room temperature for 2 hours.

Water was added, the mixture was washed with ethyl acetate, and the aqueous layer was acidified with 1 mol/L hydrochloric acid. The mixture was extracted with ethyl acetate, and the extract was washed with brine and dried over sodium sulfate. The solvent was evaporated, and the residue was recrystallized from ethanol to give Compound 15 (1.1 g, 64%) as white crystals.

Melting Point: 195–198° C.

$^1$H-NMR (DMSO-$d_6$, δ, ppm) 1.50–1.78 (m, 8H), 1.79–2.13 (m, 4H), 2.15–2.37 (m, 3H), 3.79 (s, 3H), 6.64 (d, J=9 Hz, 1H), 6.81 (d, J=9 Hz, 1H), 12.3 (br s, 1H).

MASS (m/z) 331 ($M^+$).

Elemental analysis: $C_{18}H_{21}NO_5$ Found (%) C, 65.33; H, 6.40; N, 4.27. Calcd. (%) C, 65.24; H, 6.39; N, 4.23.

Example 15

4-(8-Methoxy-1,4-benzodioxan-5-yl)-3-cyclohexenone (Compound 16)

To the mixture of Compound 2a (1.2 g, 3.6 mmol) obtained in Step A of Example 2 and p-toluenesulfonic acid monohydrate (1.2 mg, 0.0063 mmol) were added water (70 mL) and toluene (140 mL), followed by refluxing for 4 hours. The mixture was allowed to cool, the mixture was extracted with toluene, and the extract was washed with a saturated aqueous solution of sodium bicarbonate and then with brine. The mixture was dried over sodium sulfate, the solvent was evaporated, and the residue was purified by silica gel column chromatography (eluted with hexane/ethyl acetate=2/1) to give Compound 16 (0.88 g, 94%) as a pale yellow solid.

Melting Point: 56–59° C.

$^1$H-NMR (CDCl$_3$, δ, ppm) 2.59 (t, J=7 Hz, 2H), 2.75–2.85 (m, 2H), 2.97–3.10 (m, 2H), 3.88 (s, 3H), 4.25–4.37 (m, 4H), 5.83 (t, J=4 Hz, 1H), 6.48 (d, J=8 Hz, 1H), 6.81 (d, J=8 Hz, 1H).

MASS (m/z) 260 ($M^+$).

Example 16

5-(8-Methoxy-1,4-benzodioxan-5-yl)-1-indanone (Compound 17)

To a mixture of Compound A (0.30 g, 1.8 mmol) obtained in Reference Example 1 and commercially available 5-bromo-1-indanone (0.39 g, 1.8 mmol) was dissolved in DMF (3.0 ML) under a nitrogen atmosphere and were added sodium carbonate (0.39 g, 3.7 mmol) and palladium acetate (0.020 g, 0.090 mmol). The mixture was stirred at 100° C. for 2 hours, followed by stirring at 110° C. for 0.9 hour. Ethyl acetate was added to the reaction mixture, and the solid was filtered off. The resulting solution was washed with water and with brine and dried over sodium sulfate. After the solid was filtered off, the filtrate was concentrated in vacuo, and the concentrate was purified by silica gel column chromatography (eluted with hexane/ethyl acetate= 3/1) and recrystallized from acetone to give Compound 17 (0.15 g, 28%) as a white solid.

Melting Point: 168° C.

$^1$H-NMR (CDCl$_3$, δ, ppm) 2.70–2.74 (m, 2H), 3.18 (br t, 2H), 3.93 (s, 3H), 4.28–4.32 (m, 2H), 4.36–4.39 (m, 2H), 6.61 (d, J=9 Hz, 1H), 6.90 (d, J=9 Hz, 1H), 7.53 (dd, J=2, 8 Hz, 1H), 7.61 (d, J=2 Hz, 1H), 7.78 (d, J=8 Hz, 1H).

MASS (m/z) 296 ($M^+$).

Example 17

6-(8-Methoxy-1,4-benzodioxan-5-yl)-1-tetralone (Compound 18)

To a mixture of Compound A (0.37 g, 1.7 mmol) obtained in Reference Example 1 and 6-trifluoromethanesulfonyl-1-tetralone (0.51 g, 1.7mmol) [Synthetic Communication, 23(21), 2965 (1993) etc.] was dissolved in DMF (3.7 mL), and then were added sodium carbonate (0.37 g, 3.5 mmol), and palladium acetate (0.020 g, 0.090 mmol). The mixture was stirred at 100° C. for 1.5 hours, followed by stirring at 120° C. for 2.3 hours. Ethyl acetate was added to the reaction mixture, the solid was filtered off, and the resulting solution was washed with water and with brine and dried over sodium sulfate. The solid was filtered off, the filtrate was concentrated in vacuo, and the concentrate was purified by silica gel column chromatography (eluted with hexane/ ethyl acetate=3/1) and recrystallized from acetone and then from ethanol to give Compound 18 (0.070 g, 8.0%) as a white solid.

Melting Point: 156–158° C.

$^1$H-NMR (CDCl$_3$, δ, ppm) 2.12–2.21(m, 2H), 2.67(t, J=7 Hz, 2H), 3.01(t, J=6 Hz, 2H), 3.93(s, 3H), 4.28–4.31 (m, 2H), 4.36–4.38 (m, 2H), 6.59 (d, J=9 Hz, 1H), 6.88 (d, J=9 Hz, 1H), 7.39 (d, J=1 Hz, 1H), 7.46 (dd, J=2, 8 Hz, 1H), 8.06 (d, J=8 Hz, 1H).

MASS (m/z) 310 ($M^+$).

Example 18

7-(8-Methoxy-1,4-benzodioxan-5-yl)-1-benzosuberone (Compound 19)

To a mixture of Compound A (0.37 g, 1.6 mmol) obtained in Reference Example 1 and 7-bromo-1-benzosuberone (0.38 g, 1.6 mmol) was dissolved in DMF (3.3 mL) under a nitrogen atmosphere and were added sodium carbonate (0.33 g, 3.1 mmol) and palladium acetate (0.020 g, 0.080 mmol). The mixture was stirred at 100° C. for 6.5 hours, ethyl acetate was added to the reaction mixture, and the solid was filtered off. The resulting solution was washed with water and with brine and dried over sodium sulfate. The solid was filtered off, the filtrate was concentrated in vacuo, and the concentrate was purified by silica gel column chromatography (eluted with hexane/ethyl acetate=3/1) and recrystallized from ethanol and then from acetone to give Compound 19 (0.16 g, 32%) as a white solid.

Melting Point: 124–126° C.

$^1$H-NMR (CDCl$_3$, δ, ppm) 1.83–1.94 (m, 4H), 2.74–2.78 (m, 2H), 2.96–3.01 (m, 2H), 3.93 (s, 3H), 4.28–4.31 (m, 2H), 4.36–4.39 (m, 2H), 6.59 (d, J=9 Hz, 1H), 6.89 (d, J=9 Hz, 1H), 7.36 (d, J=2 Hz, 1H), 7.47 (dd, J=2, 8 Hz, 1H), 7.79 (d, J=8 Hz, 1H).

MASS (m/z) 324 ($M^+$).

Example 19

Ethyl 2-[4-cyano-4-(8-methoxy-1,4-benzodioxan-5-yl)cyclohexan-1-yl]acetate (Compound 20)

To a solution of Compound 10 (0.55 g, 1.5 mmol) obtained in Example 10 in ethanol (5.5 mL) and acetone (8.0 m) was added 10% palladium-carbon (containing 50% of water) (0.11 g), and the mixture was subjected to a hydrogenation reaction at room temperature and ordinary pressure for 3 hours. After removal of the catalyst, the solvent was evaporated in vacuo from the filtrate to give Compound 20 (0.54 g, 100%) as a mixture of isomers in a pale yellow oil.

NMR (CDCl$_3$, δ, ppm) 1.18–1.33 (m, 3H), 1.45–1.73 (m, 3H), 1.77–1.97(m, 4H), 2.25–2.42 (m, 4H), 3.87 and 3.88 (each s, total 3H), 4.04–4.27 (m, 2H), 4.35(s, 4H), 6.48 and 6.49 (each d, J=9 Hz, total 1H), 6.84 and 6.88 (each d, J=9 Hz, total 1H).

MASS (m/z) 359 ($M^+$).

Example 20

2-[4-Cyano-4-(8-methoxy-1,4-benzodioxan-5-yl)cyclohexan-1-yl]acetic acid (Compound 21)

To a solution of Compound 20 (0.41 g, 1.1 mmol) obtained in Example 19 in ethanol (4.1 mL) was added a 2 mol/L aqueous solution of sodium hydroxide (1.1 mL), and the mixture was stirred at room temperature for 1 hour and then stirred at 60° C. for 20 minutes. The mixture was allowed to cool, and water and ethyl acetate were added to the mixture, followed by separating into an organic layer and an aqueous layer. The aqueous layer was acidified with 6 mol/L aqueous hydrochloric acid and extracted with ethyl acetate, and the extract was washed with brine and dried over sodium sulfate. The solvent was evaporated in vacuo, toluene was added to the residue, and the mixture was evaporated in vacuo. To the residue was added diisopropyl ether, and the precipitated solid was collected by filtration and recrystallized from ethanol to give Compound 21 (0.13 g, 36%) as a mixture of isomers in white crystals.

Melting Point: 149–150° C.

NMR (DMSO-$d_6$, δ, ppm) 1.25–1.57 (m, 2H), 1.63–1.95 (m, 5H), 2.08–2.35 (m, 4H), 3.74 (s, 3H), 4.15–4.42 (m, 4H), 6.59 (d, J=9 Hz, 1H), 6.81 and 6.86 (each d, J=9 Hz, total 1H), 12.1 (s, 1H).

MASS (m/z) 359 ($M^+$).

Example 21

4-(8-Methoxy-1,4-benzodioxan-5-yl)-1(3H)-isobenzofuranone (Compound 22)

To ethyl 4-(8-methoxy-1,4-benzodioxan-5-yl)-2-acetoxymethylbenzoate (0.61 g) which was obtained by treating Compound A (0.40 g, 1.9 mmol) obtained in Reference Example 1 and Compound C (0.57 g, 1.9 mmol) obtained in Reference Example 3 in the same manner as in Example 17 were added ethanol (6.0 mL) and a 5 mol/L solution of potassium hydroxide (1.2 mL) and the mixture was stirred at room temperature for 35 minutes. The mixture was evaporated in vacuo, and water was added to the residue. To the resulting solution was added 6 mol/L hydrochloric acid to adjust it to pH 2, and the precipitated solid was collected by filtration and dried in vacuo to give a white solid (0.46 g).

To this solid was added acetic acid(4.2 mL), followed by stirring at 90° C. To the reaction mixture was added a saturated aqueous solution of sodium bicarbonate so that acetic acid was neutralized, and the mixture was extracted with ethyl acetate. The organic layer was washed with a saturated aqueous solution of sodium bicarbonate and brine and dried over magnesium sulfate. The solid was filtered off, the filtrate was concentrated in vacuo, and the concentrate was purified by silica gel column chromatography (eluted with hexane/ethyl acetate=3/2) and recrystallized from ethanol to give Compound 22 (0.33 g, 70%) as a white solid.

Melting Point: 158–160° C.

NMR (CDCl$_3$, δ, ppm) 3.94 (s, 3H), 4.28–4.32 (m, 2H), 4.37–4.40 (m, 2H), 5.35 (s, 2H), 6.62 (d, J=8.6 Hz, 2H), 6.89 (d, J=8.6 Hz, 2H), 7.62 (s, 1H), 7.67 (d, J=8.3 Hz, 1H), 7.93 (d, J=8.3 Hz, 1H).

MASS(m/z) 298($M^+$).

Elemental analysis: $C_{17}H_{14}O_5$ Found (%) C, 68.55; H, 4.61. Calcd. (%) C, 68.45; H, 4.73.

Example 22

4-(8-Methoxy-1,4-benzodioxan-5-yl)phthalimide (Compound 23)

To Compound B (0.12 g, 0.4 mmol) obtained in Reference Example 2 were added ethylene glycol (0.6 mL) and urea (0.02 g, 0.4 mmol) under argon atmosphere, followed by stirring at 150° C. for 5.3 hours. To the reaction mixture was added ethanol at room temperature, and the precipitated solid was collected by filtration and dried in vacuo to give Compound 23 (0.08 g, 73%) as a yellow solid.

Melting Point: 285–287° C.

NMR (CDCl$_3$, δ, ppm) 3.94 (s, 3H), 4.29–4.32 (m, 2H), 4.37–4.40 (m, 2H), 6.62 (d, J=8.6 Hz, 1H), 6.91 (d, J=8.6 Hz, 1H), 7.27 (br s, 1H), 7.84–7.88 (br t, 2H), 8.04 (s, 1H).

MASS(m/z) 311($M^+$).

Elemental analysis: $C_{17}H_{13}NO_5$ Found (%) C, 65.49; H, 4.25; N, 4.22. Calcd. (%) C, 65.59; H, 4.21; N, 4.50.

Example 23

Ethyl cis-4-cyano-4-(3,4-dihydro-9-methoxy-2H-1,5-benzodioxepin-6-yl)cyclohexanecarboxylate (Compound 24)

(Step A) Synthesis of ethyl 4-hydroxy-4-(3,4-dihydro-9-methoxy-2H-1,5-benzodioxepin-6-yl)cyclohexanecarboxylate (Compound 24a)

To a solution of 9-bromo-3,4-dihydro-6-methoxy-2H-1,5-benzodioxepine (25.7g, 99.2mmol) in THF (154mL) was added dropwise a 1.5 mol/L solution of n-butyl lithium in hexane (69 mL, 104 mmol) at −78° C., and the mixture was stirred at −78° C. for 10 minutes.

The reaction mixture was added dropwise to a solution of ethyl 4-cyclohexanonecarboxylate (20.5 mL, 129 mmol) in THF (385 mL) at −78° C., followed by stirring at −78° C. for 1 hour. The reaction mixture was added to an aqueous solution of ammonium chloride while adjusting the mixture to pH 7 with 6 mol/L hydrochloric acid, and water was added. The mixture was extracted with ethyl acetate, the extract was washed with water and brine and dried over magnesium sulfate. The solid was filtered off, the solvent was evaporated, and the residue was purified by silica gel column chromatography (eluted with hexane/ethyl acetate= 3/1→2/1) to give Compound 24a (12.9 g, 40%) as a pale yellow oil (a mixture of isomers).

$^1$H-NMR (CDCl$_3$, δ, ppm) 1.2–1.3 (m, 3H), 1.7–2.6 (m, 11H), 3.65 and 3.69 (each s, total 1H), 3.83 (s, 3H), 4.1–4.2 (m, 2H), 4.2–4.4 (m, 4H), 6.54 and 6.55 (each d, J=9 Hz, total 1H), 6.91 and 6.92 (each d, J=9 Hz, total 1H).

MASS (m/z) 330 [$(M+H)^+$].

(Step B) Synthesis of Compound 24

To a solution of Compound 24a (7.36 g, 21.0 mmol) obtained in Step A in dichloromethane (74 mL) was added trimethylsilyl cyanide (5.6 mL, 42 mmol) followed by cooling the mixture to −78° C., and boron trifluoride-ethyl ether complex (2.1 mL, 17 mmol) was added dropwise. The mixture was stirred at −78° C. for 50 minutes followed by stirring at 0° C. for 30 minutes. To the mixture was added a saturated aqueous solution of sodium bicarbonate, and the organic layer was washed with water and brine and dried over magnesium sulfate. The solid was filtered off, the solvent was evaporated, and the residue was purified by silica gel column chromatography (eluted with hexane/ethyl acetate=3/1→30/11) and recrystallized from ethanol to give Compound 24 (2.04 g, 27%) as a white solid.

Melting Point: 117–118° C.

$^1$H-NMR (CDCl$_3$, δ, ppm) 1.30(t, J=7 Hz, 3H), 1.6–2.5 (m, 11H), 3.86 (s, 3H), 4.17 (q, J=7 Hz, 3H), 4.2–4.3 (m, 4H), 6.58 (d, J=9 Hz, 1H), 6.86 (d, J=9 Hz, 1H).
MASS(m/z) 360[(M+H)$^+$].

Example 24 cis-4-Cyano-4-(3,4-dihydro-9-methoxy-2H-1,5-benzodioxepin-6-yl)cyclohexanecarboxylic acid (Compound 25)

To a mixture of Compound 24 (1.53 g, 4.26 mmol) obtained in Example 23 and ethanol (15 mL) was added dropwise a 2 mol/L aqueous solution of sodium hydroxide (21 mL) followed by stirring at room temperature for 4.6 hours. The mixture was cooled to 0° C. and acidified with 6 mol/L hydrochloric acid, and the precipitated solid was collected by filtration and re-slurried with ethanol to give Compound 25 (1.35 g, 96%) as a white solid.

Melting Point: 274–275° C.
$^1$H-NMR (DMSO-d$_6$, δ, ppm) 1.6–2.4 (m, 11H), 3.75 (s, 3H), 4.0–4.2 (m, 4H), 6.74 (d, J=9 Hz, 1H), 6.93 (d, J=9 Hz, 1H), 12.26(brs, 1H).
MASS(m/z) 330[(M–H)$^-$].
Elemental analysis: C$_{18}$H$_{21}$NO$_5$ Found (%) C, 65.24; H, 6.39; N, 4.23. Calcd. (%) C, 65.41; H, 6.33; N, 4.24.

Example 25

Ethyl cis-4-cyano-4-(7-methoxy-1,3-benzodioxol-4-yl)cyclohexanecarboxylate (Compound 26) (Step A) Synthesis of ethyl 4-hydroxy-4-(7-methoxy-1,3-benzodioxol-4-yl)cyclohexanecarboxylate (Compound 26a)

To a solution of 7-bromo-4-methoxy-1,3-benzodioxole (6.17 g, 19.1 mmol) in THF (135 mL) was added dropwise a 1.5 mol/L solution of n-butyl lithium in hexane (27 mL, 41 mmol) at –78° C., followed by stirring at –78° C. for 10 minutes. To a solution of ethyl 4-cyclohexanonecarboxylate (8.1 mL, 51 mmol) in THF (135 mL) was added dropwise this reaction mixture at –78° C., followed by stirring at –78° C. for 30 minutes. To an aqueous solution of ammonium chloride was added to this reaction mixture. The mixture was adjusted to pH 7 with 6 mol/L hydrochloric acid, and water was added. The mixture was extracted with ethyl acetate, and the extract was washed with water and brine and dried over magnesium sulfate. The solid was filtered off, the solvent was evaporated, and the residue was purified by silica gel column chromatography (eluted with hexane/ethyl acetate=5/1→3/1) to give Compound 26a (6.73 g, 54%) as a pale yellow oil (a mixture of isomers).

$^1$H-NMR (CDCl$_3$, δ, ppm) 1.2–1.3 (m, 3H), 1.7–2.7 (m, 9H), 3.89 (s, 3H), 4.1–4.2 (m, 2H), 5.97 and 5.97 (each s, total 1H), 6.50 and 6.51 (each d, J=9 Hz, total 1H), 6.84 and 6.88 (each d, J=9 Hz, total 1H)(A proton of hydroxy is not found).

MASS(m/z) 323[(M+H)$^+$].
(Step B) Synthesis of Compound 26

To a solution of Compound 26a (6.17 g, 19.1 mmol) obtained in Step A in dichloromethane (62 mL) was added trimethylsilyl cyanide(5.1 mL, 38 mmol). To this mixture was added dropwise boron trifluoride-ethyl ether complex (1.9 mL, 15 mmol) at –78° C., and the mixture was stirred at –78° C. for 55 minutes followed by stirring at 0° C. for 25 minutes. A saturated aqueous sodium bicarbonate was added, and the organic layer was washed with water and with brine and dried over magnesium sulfate. The solid was filtered off, the solvent was evaporated from the filtrate, and the residue was purified by silica gel column chromatography (eluted with hexane/ethyl acetate=3/1) and recrystallized from ethanol to give Compound 26 (2.39 g, 38%) as a white solid.

Melting Point: 109–112° C.
$^1$H-NMR (CDCl$_3$, δ, ppm) 1.27 (t, J=7 Hz, 3H), 1.9–2.4 (m, 9H), 3.90 (s, 3H), 4.16 (q, J=7 Hz, 2H), 6.01 (s, 2H), 6.53 (d, J=9 Hz, 1H), 6.96 (d, J=9 Hz, 1H),
MASS(m/z) 331(M$^+$).

Example 26 cis-4-Cyano-4-(7-methoxy-1,3-benzodioxol-4-yl) cyclohexanecarboxylic acid (Compound 27)

To a mixture of Compound 26 (0.60 g, 1.8 mmol) obtained in Example 25 and ethanol (12 mL) was added dropwise a 2 mol/L aqueous solution of sodium hydroxide (3.6 mL) followed by stirring at room temperature for 1.7 hours. Ethanol was evaporated in vacuo, and the mixture was cooled to 0° C. and acidified with 6 mol/L hydrochloric acid. The precipitated solid was collected by filtration and recrystallized from ethanol to give Compound 27 (0.50 g, 92%) as a white solid.

Melting Point: 206–208° C.
$^1$H-NMR (DMSO-d$_6$, δ, ppm) 1.6–2.4 (m, 9H), 3.82 (s, 3H), 6.05 (s, 2H), 6.70 (d, J=9 Hz, 1H), 6.87 (d, J=9 Hz, 1H), 12.30(brs, 1H).
MASS(m/z) 302[(M–H)$^-$].
Elemental analysis: C$_{16}$H$_{17}$NO$_5$ Found (%) C, 63.36; H, 5.65; N, 4.62. Calcd. (%) C, 63.48; H, 5.76; N, 4.50.

Example 27 cis-4-Cyano-4-(8-hydroxy-1,4-benzodioxan-5-yl) cyclohexanecarboxylic acid (Compound 28)

To a suspension of Compound 5 (1.80 g, 5.67 mmol) obtained in Example 5 in dichloromethane (57 mL) was added dropwise a 1 mol/L solution of boron tribromide in dichloromethane (11.3 mL, 11.3 mmol) at 6° C. followed by stirring at room temperature overnight. The reaction mixture was cooled to 5° C., and water (57 mL) was added to the mixture. The precipitated solid was collected by filtration and dried in vacuo to give Compound 28 (916 mg, 53%) as an ash-colored solid.

Melting Point: 258–260° C.
$^1$H-NMR (CDCl$_3$, δ, ppm) 1.6–2.5 (m, 9H), 4.2–4.3 (m, 4H), 6.40(d, J=9 Hz, 1H), 6.64 (d, J=9 Hz, 1H), 9.29 (s, 1H), 12.24 (brs, 1H).
MASS(m/z) 302[(M–H)$^-$].

Example 28

Ethyl cis-4-cyano-4-(8-hydroxy-1,4-benzodioxan-5-yl)cyclohexanecarboxylate (Compound 29)

To a suspension of Compound 28 (682 mg, 2.25 mmol) obtained in Example 27 in ethanol (6.8 mL) was added a 4 mol/L solution of hydrogen chloride in ethyl acetate (0.5 mL, 2.0 mmol) followed by stirring at room temperature for 2 days. Water (30 mL) was added to the mixture, and the precipitated solid was collected by filtration and dried in vacuo to give Compound 29 (634 mg, 85%) as a white solid.

Melting Point: 136° C.
$^1$H-NMR (CDCl$_{31}$ δ, ppm) 1.30 (t, J=7 Hz, 3H), 1.7–2.5 (m, 9H), 4.15 (q, J=7 Hz, 2H), 4.3–4.4 (m, 4H), 5.40 (s, 1H), 6.52 (d, J=9 Hz, 1H), 6.78 (d, J=9 Hz, 1H).

Example 29

Ethyl cis-4-cyano-4-(8-difluoromethoxy-1,4-benzodioxan-5-yl)cyclohexanecarboxylate (Compound 30)

A mixture of Compound 29 (500 mg, 1.51 mmol) obtained in Example 28, chlorodifluoromethyl acetate(436 mg, 3.02 mmol) potassium carbonate (438 mg, 3.17 mmol), and DMF (1.0 mL) was stirred at 80° C. for 0.4 hour followed by stirring at 90° C. for 3 hours. To the mixture was added DMF (2.0 mL) followed by stirring at 90° C. for 2.8 hours. The reaction mixture was cooled to room temperature, 1 mol/L hydrochloric acid was added thereto to neutralize it, and ethyl acetate was added thereto for partition. The organic layer was washed with water twice and with brine twice and dried over magnesium sulfate. The solid was filtered off, the solvent was evaporated from the resulting solution, and the residue was purified by silica gel column chromatography (eluted with hexane/ethyl acetate= 1/1) to give Compound 30 (97 mg, 79%) as a colorless oil.

$^1$H-NMR (CDCl$_3$, δ, ppm) 1.28 (t, J=7 Hz, 3H), 1.7–2.6 (m, 9H), 4.15 (q, J=7 Hz, 2H), 4.3–4.4 (m, 4H), 6.55 (t, J=75 Hz, 1H), 6.76 (d, J=9 Hz, 1H), 6.86 (d, J=9 Hz, 1H).

Example 30 cis-4-Cyano-4-(8-difluoromethoxy-1,4-benzodioxan-5-yl)cyclohexanecarboxylic acid (Compound 31)

To a solution of Compound 30 (90 mg, 0.24 mmol) obtained in Example 29 in ethanol (1.8 mL) was added dropwise a 6 mol/L aqueous solution of potassium hydroxide (0.36 mL, 2.16 mmol) followed by stirring at room temperature for 6 hours. To the reaction mixture was added water, and 6 mol/L hydrochloric acid was added thereto to adjust the mixture to pH 1. The precipitated solid was collected by filtration and dried in vacuo to give Compound 31 (73 mg, 88%) as a white solid.

Melting Point: 208–213° C.

$^1$H-NMR (CDCl$_3$, δ, ppm) 1.8–2.5 (m, 9H), 4.3–4.5 (m, 4H), 6.55 (t, J=74 Hz, 1H), 6.77 (d, J=9 Hz, 1H), 6.87 (d, J=9 Hz, 1H)(A proton of carboxy is not found).

MASS(m/z) 352[(M−H)$^-$].

Reference Example 1

8-Methoxy-1,4-benzodioxane-5-boric acid (Compound A)

To a solution of 5-bromo-8-methoxy-1,4-benzodioxane (7.4 g, 30 mmol) in THF (74 mL) was added dropwise a 1.54 mol/L solution of n-butyl lithium in hexane (23 mL, 35 mmol) at −78° C., followed by stirring at −78° C. for 0.5 hour.

To this reaction mixture was added a solution of trimethyl borate (4.8 mL, 42 mmol) in THF (15 mL) at −78° C., and the mixture was stirred for 1.7 hours, followed by stirring for 1.8 hours at room temperature. Hydrochloric acid was added to adjust the mixture to pH 1, the mixture was extracted with ethyl acetate, and the extract was washed with water and brine and dried over magnesium sulfate. The solid was filtered off, and the solvent was evaporated in vacuo, followed by recrystallization from toluene to give Compound A (4.35 g, 68%) as a milky white solid.

Melting Point: >300° C.

$^1$H-NMR (CDCl$_3$, δ, ppm) 3.91 (s, 3H), 4.34–4.41 (m, 4H), 5.73 (s, 2H), 6.59 (d, J=8 Hz, 1H), 7.37 (d, J=8 Hz, 1H).

MASS (m/z) 210 (M$^+$).

Reference Example 2

4-(8-Methoxy-1,4-benzodioxan-5-yl)phthalic acid (Compound B)

To a mixture of diethyl 4-(8-methoxy-1,4-benzodioxan-5-yl)phthalate (0.69 g, 1.8 mmol) obtained by treating Compound A (0.70 g, 3.3 mmol) obtained in Reference Example 1 and known diethyl 4-bromophthalate (1.00 g, 3.3 mmol) by the same reaction as in Example 17 were added ethanol (7.0 mL) and a 6 mol/L aqueous solution of potassium hydroxide (1.4 mL), the mixture was stirred at room temperature for 2 hours, and then ethanol was evaporated in vacuo. Water was added to the resulting solution, the mixture was adjusted to pH 2 with 6 mol/L hydrochloric acid, and the precipitated solid was collected by filtration and dried in vacuo to give Compound B (0.55 g, 94%) as a white solid.

Melting Point: 192–196° C.

NMR (DMSO-d$_6$, δ, ppm) 3.79 (s, 3H), 4.26 (s, 4H), 4.37–4.40 (m, 2H), 6.69 (d, J=8.6 Hz, 1H), 6.89 (d, J=8.6 Hz, 1H), 7.63–7.72 m, 3H), 13.07 (br s, 1H).

MASS(m/e) 312(M$^+$−H$_2$O).

Reference Example 3

Ethyl 2-acetoxymethyl-4-bromobenzoate (Compound C)

(Step A) Ethyl 4-bromo-2-bromomethylbenzoate (Compound Ca)

To a mixture of ethyl 4-bromo-2-methylbenzoate (10.0 g, 41 mmol) and α,α,α-trifluorotoluene (300 mL) were added N-bromosuccinimide (7.54 g, 42 mmol) and azobisisobutyronitrile (2.0 g, 12 mmol), followed by stirring at 80° C. for 5.5 hours. Water was added to the reaction mixture for partition, and the organic layer was washed with water and brine and dried over magnesium sulfate. The solid was filtered off, the filtrate was concentrated in vacuo, and the concentrate was purified by silica gel column chromatography (eluted with hexane/ethyl acetate=20/1), followed by recrystallization from hexane to give Compound Ca(4.07 g,31%) as a white solid.

Melting Point: 56.0–57.0° C.

NMR (CDCl$_3$, δ, ppm) 1.42 (t, J=7.1 Hz, 3H), 4.40 (q, J=7.1 Hz, 2H), 4.89 (s, 2H), 7.50 (dd, J=2.0, 8.4 Hz, 1H), 7.62 (d, J=2.0 Hz, 1H), 7.84 (d, J=8.4 Hz, 1H).

MASS(m/e) 300(M$^+$), 300(M$^+$+2), 300(M$^+$+4).

(Step B) Compound C

To a mixture of Compound Ca (1.0 g, 3.2 mmol) and acetic acid (10 mL) was added sodium acetate (4.0 g, 49 mmol), followed by stirring at 120° C. for 0.5 hour. A saturated aqueous solution of sodium bicarbonate was added to the reaction mixture so that acetic acid was neutralized, and then ethyl acetate was added for partition. The organic layer was washed with a saturated aqueous solution of sodium bicarbonate and then with brine and dried over magnesium sulfate. The solid was filtered off, the filtrate was concentrated in vacuo, and the concentrate was purified by silica gel column chromatography (eluted with hexane/ethyl acetate=25/1) to give Compound C (0.69 g, 71%) as a white solid.

Melting Point: 51.5–52.5° C.

NMR (CDCl$_3$, δ, ppm) 1.39 (t, J=7.1 Hz, 3H), 2.17 (s, 3H), 4.36 (q, J=7.1 Hz, 2H), 5.50 (s, 2H), 7.51 (dd, J=2.0, 8.4 Hz, 1H), 7.65 (d, J=2.0 Hz, 1H), 7.87 (d, J=8.4 Hz, 1H).

MASS(m/e) 300(M$^+$), 300(M$^+$+2).

INDUSTRIAL APPLICABILITY

According to the present invention, there can be provided oxygen-containing heterocyclic compounds which have phosphodiesterase (PDE) IV inhibitory activity and which are useful as a therapeutic agent for inflammatory allergic diseases such as bronchial asthma, allergic rhinitis, atopic dermatitis and nephritis; autoimmune diseases such as chronic obstructive pulmonary disease, rheumatism, multiple sclerosis, Crohn's disease, psoriasis and systemic lupus erythematosus; diseases of the central nervous system such as depression, amnesia and dementia; organopathy associated with ischemia-reperfusion caused by cardiac failure, shock and cerebrovascular disease, and the like; insulin-resistant diabetes; wounds; AIDS; osteoporosis; urinary calculus; urinary incontinence and the like; or as a recuperative agent for fatigue, malaise and the like.

What is claimed is:

1. An oxygen-containing heterocyclic compound represented by the following formula (I):

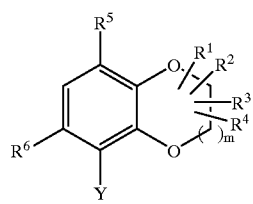

(I)

wherein m represents an integer of 0 to 4;

$R^1$, $R^2$, $R^3$ and $R^4$ independently represent a hydrogen atom, substituted or unsubstituted lower alkyl, substituted or unsubstituted cycloalkyl, polycycloalkyl, substituted or unsubstituted lower alkoxycarbonyl, substituted or unsubstituted lower alkanoyl, substituted or unsubstituted lower alkanoyloxy, cyano, hydroxy, substituted or unsubstituted lower alkoxy, substituted or unsubstituted lower alkenyl, substituted or unsubstituted cycloalkenyl, substituted or unsubstituted aryl, a substituted or unsubstituted aromatic hetecyclic group, substituted or unsubstituted aralkyl, or —$CONR^7R^8$ wherein $R^7$ and $R^8$ independently represent a hydrogen atom, substituted or unsubstituted lower alkyl, substituted or unsubstituted lower alkanoyl, substituted or unsubstituted cycloalkyl, substituted or unsubstituted aryl, a substituted or unsubstituted aromatic heterocyclic group or substituted or unsubstituted aralkyl, or $R^7$ and $R^8$ are combined to represent a substituted or unsubstituted heterocyclic group together with the adjacent nitrogen atom; two groups present on the same carbon atom among $R^1$, $R^2$, $R^3$ and $R^4$ are combined to represent a saturated Spiro carbon ring together with the said carbon atom; two groups present on the adjacent carbon atoms among $R^1$, $R^2$, $R^3$ and $R^4$ are combined to represent a saturated carbon ring together with the said adjacent two carbon atoms; two groups present on the adjacent carbon atoms among $R^1$, $R^2$, $R^3$ and $R^4$ are combined to represent a single bond forming a double bond together with the already-existing bond;

$R^5$ represents hydroxy, or substituted or unsubstituted lower alkoxy;

$R^6$ represents a hydrogen atom or halogen;

Y represents the following formula (II):

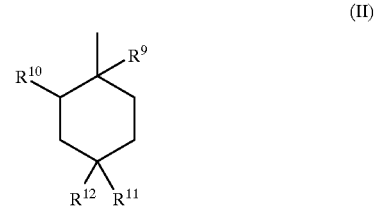

(II)

wherein $R^9$ represents cyano, ethynyl or carbamoyl, and $R^{10}$ represents a hydrogen atom, or $R^9$ and $R^{10}$ are combined to represent a single bond forming a double bond together with the already-existing bond, $R^{11}$ represents hydroxy, formyl, substituted or unsubstituted lower alkoxy, substituted or unsubstituted tetrazolyl, —$NR^{13}R^{14}$ wherein $R^{13}$ and $R^{14}$ independently represent a hydrogen atom, substituted or unsubstituted lower alkyl, substituted or unsubstituted lower alkanoyl, substituted or unsubstituted cycloalkyl, substituted or unsubstituted aryl, a substituted or unsubstituted aromatic heterocyclic group or substituted or unsubstituted aralkyl, or $R^{13}$ and $R^{14}$ are combined to represent a substituted or unsubstituted heterocyclic group together with the adjacent nitrogen atom, —$COOR^{15}$ wherein $R^{15}$ represents a hydrogen atom, or substituted or unsubstituted lower alkyl, —$CONR^{16}R^{17}$ wherein $R^{16}$ and $R^{17}$ independently represent a hydrogen atom, substituted or unsubstituted lower alkyl, substituted or unsubstituted lower alkanoyl, substituted or unsubstituted cycloalkyl, substituted or unsubstituted aryl, a substituted or unsubstituted aromatic heterocyclic group, or substituted or unsubstituted aralkyl, or $R^{16}$ and $R^{17}$ are combined to represent a substituted or unsubstituted heterocyclic group together with the adjacent nitrogen atom, or —$CH_2COOR^{18}$ wherein $R^{18}$ represents a hydrogen atom or substituted or unsubstituted lower alkyl, $R^{12}$ represents a hydrogen atom, or substituted or unsubstituted lower alkoxy, or $R^{11}$ and $R^{12}$ are combined together to represent —$OCH_2(CH_2)_pO$— wherein p represents an integer of 1 to 3, —$CR^{19}R^{20}O$— wherein $R^{19}$ and $R^{20}$ independently represent a hydrogen atom or cyano, =$CHOR^{21}$ wherein $R^{21}$ represents substituted or unsubstituted lower alkyl, substituted or unsubstituted lower alkenyl, or substituted or unsubstituted aralkyl, =$CHCOOR^{22}$ wherein $R^{22}$ represents a hydrogen atom, or substituted or unsubstituted lower alkyl or =O; the following formula (III):

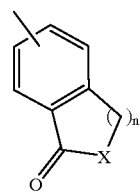

(III)

wherein n represents an integer of 0 to 4, X represents $CH_2$, $NR^{23}$ wherein $R^{23}$ represents a hydrogen atom, substituted or unsubstituted lower alkyl, substituted or unsubstituted lower alkanoyl, substituted or unsubstituted cycloalkyl, substituted or unsubstituted aryl, a substituted or unsubstituted aromatic heterocyclic group, or substituted or unsubstituted aralkyl or O; the following formula (IV):

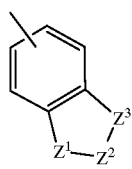

(IV)

wherein $Z^1$—$Z^2$—$Z^3$ represents O—N=CH, S—N=CH, O—CH=CH, S—CH=CH, N=CH—S, N=CH—O, C(=O)—NH—NH, C(=O)—N=N, C(=O)—CH$_2$—C(=O), C(=O)—NR$^a$—C(=O) wherein R$^a$ represents a hydrogen atom, substituted or unsubstituted lower alkyl, or substituted or unsubstituted aralkyl or CH$_2$—NR$^b$—C(=O) wherein R$^b$ represents a hydrogen atom, substituted or unsubstituted lower alkyl, or substituted or unsubstituted aryl; 2,1,3-benzothiadiazolyl; or 2,1,3-benzofurazanyl; or a pharmaceutically acceptable salt thereof.

2. The oxygen-containing heterocyclic compound according to claim 1, wherein Y is the formula (II), or a pharmaceutically acceptable salt thereof.

3. The oxygen-containing heterocyclic compound according to claim 2, wherein R$^9$ is cyano, or a pharmaceutically acceptable salt thereof.

4. The oxygen-containing heterocyclic compound according to any one of claims 1 to 3, wherein m is 0 to 2, or a pharmaceutically acceptable salt thereof.

5. The oxygen-containing heterocyclic compound according to any claims 1 to 3, wherein all of R$^1$, R$^2$, R$^3$ and R$^4$ are hydrogen atoms, or one group among R$^1$, R$^2$, R$^3$ and R$^4$ is substituted or unsubstituted lower alkyl while other three groups are hydrogen atoms, or a pharmaceutically acceptable salt thereof.

6. The oxygen-containing heterocyclic compound according to any one of claims 1 to 3, wherein R$^{11}$ represents carboxy or hydroxy, or R$^{11}$ and R$^{12}$ are combined together to represent =O, or a pharmaceutically acceptable salt thereof.

7. The oxygen-containing heterocyclic compound according to claim 1, wherein Y is the formula (III), or a pharmaceutically acceptable salt thereof.

8. The oxygen-containing heterocyclic compound according to claim 7, wherein n is 1, or a pharmaceutically acceptable salt thereof.

9. The oxygen-containing heterocyclic compound according to claim 7 or 8, wherein X is CH$_2$, or a pharmaceutically acceptable salt thereof.

10. A method of inhibiting phosphodiesterase (PDE) IV, which comprises administering an effective dose of at least one oxygen-containing heterocyclic compound according to any one of claims 1–3, 7 or 8 or a pharmaceutically acceptable salt thereof.

11. A pharmaceutical composition comprising an effective amount of at least one oxygen-containing heterocyclic compound according to any one of claims 1 to 3, 7 or 8 or pharmaceutically acceptable salt thereof together with a pharmaceutically acceptable carrier or diluent.

* * * * *

UNITED STATES PATENT AND TRADEMARK OFFICE
CERTIFICATE OF CORRECTION

PATENT NO. : 6,376,535 B2
DATED : April 23, 2002
INVENTOR(S) : Etsuo Ohshima et al.

It is certified that error appears in the above-identified patent and that said Letters Patent is hereby corrected as shown below:

Column 1,
Line 28, "CAMP" should read -- cAMP --;
Line 56, "declines" should read -- suppresses --.

Column 2,
Line 62, "CAMP" should read -- cAMP --.

Column 3,
Line 22, "hetecyclic" should read -- heterocyclic --;
Line 34, "Spiro" should read -- spiro --.

Column 22,
Line 46, "similarly" should read -- similar --;
Line 53, "process" should read -- processes --.

Column 31,
Line 57, "15" should be deleted;
Line 61, "mol/L." should read -- µmol/L. --.

Column 33,
Line 2, "(I).or" should read -- (I) or --.

Column 34,
Line 9, "added water," should read -- water was added, --.

Column 39,
Line 2, "for18" should read -- for 18 --.

Column 41,
Line 40, "To a" should read -- A --.
Line 43, "were" should read -- then there were --;
Line 65, "To a" should read -- A --.

Column 42,
Line 27, "To a" should read -- A --;
Line 30, "were" should read -- then there were --.

UNITED STATES PATENT AND TRADEMARK OFFICE
CERTIFICATE OF CORRECTION

PATENT NO. : 6,376,535 B2
DATED : April 23, 2002
INVENTOR(S) : Etsuo Ohshima et al.

It is certified that error appears in the above-identified patent and that said Letters Patent is hereby corrected as shown below:

Column 45,
Line 42, "To an" should read -- An --;

Column 49,
Line 44, "hetecyclic" should read -- heterocyclic --;
Line 56, "Spiro" should read -- spiro --.

Signed and Sealed this

Sixth Day of August, 2002

Attest:

JAMES E. ROGAN
Attesting Officer
Director of the United States Patent and Trademark Office